US011771750B2

(12) United States Patent
Lin et al.

(10) Patent No.: US 11,771,750 B2
(45) Date of Patent: *Oct. 3, 2023

(54) **COMPOSITION AND METHOD FOR GENERATING IMMUNITY TO *BORRELIA BURGDORFERI***

(71) Applicant: Health Research, Inc., Menands, NY (US)

(72) Inventors: Yi-Pin Lin, Cohoes, NY (US); Kaspars Tars, Viksnas (LV)

(73) Assignees: HEALTH RESEARCH, INC., Menands, NY (US); LATVIAN BIOMEDICAL RESEARCH AND STUDY CENTER, Riga (LV)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,461

(22) Filed: Mar. 28, 2022

(65) Prior Publication Data

US 2022/0280627 A1   Sep. 8, 2022

Related U.S. Application Data

(63) Continuation of application No. 16/891,147, filed on Jun. 3, 2020, now Pat. No. 11,285,198, which is a continuation of application No. 16/229,452, filed on Dec. 21, 2018, now Pat. No. 10,695,413.

(60) Provisional application No. 62/611,212, filed on Dec. 28, 2017.

(51) Int. Cl.
*A61K 39/02* (2006.01)
*A61P 31/04* (2006.01)
*A61K 39/00* (2006.01)

(52) U.S. Cl.
CPC .......... *A61K 39/0225* (2013.01); *A61P 31/04* (2018.01); *A61K 2039/5258* (2013.01); *A61K 2039/55566* (2013.01)

(58) Field of Classification Search
None
See application file for complete search history.

(56) References Cited

U.S. PATENT DOCUMENTS

| | | |
|---|---|---|
| 8,247,181 B2 | 8/2012 | Barbour |
| 9,182,412 B2 | 11/2015 | Barbour |
| 2012/0142023 A1 | 6/2012 | Ascoli |
| 2013/0210651 A1 | 8/2013 | Barbour |
| 2014/0308677 A1 | 10/2014 | Ascoli |
| 2019/0201516 A1 | 7/2019 | Lin et al. |
| 2020/0323972 A1 | 10/2020 | Lin |

OTHER PUBLICATIONS

Siegel et al., "Deciphering the Ligand-bind Sites in the Borrelia burgdorferi Complement Regulator-acquiring Surface Protein 2 Required for Interactions with the Human Immune Regulators Factor H and Factor H-like Protein 1", Dec. 12, 2008, vol. 283, No. 50, pp. 34855-34863, The Journal of Biological Chemistry, Jena, Germany.

Hartmann et al., "Functional characterization of BbCRASP-s, a distinct outer membrane protein of Borrelia burgdorferi that binds host complement regulators factor H and FHL-1", Aug. 1, 2006, 61(5), 1220-1236, Molecular Microbiology, Lexington, Kentucky.

Kang et al., "Enhancement of Mucosal Immunization with Virus-Like Particles of Simian Immunodeficiency Virus", Mar. 2003, p. 3615-3623, vol. 77, No. 6, Journal of Virology, American Society for Microbiology, Atlanta, Georgia.

Khan et al., "Head-to-Head Comparison of Soluble vs. QB VLP Circumsporozoite Protein Vaccines Reveals Selective Enhancement of NANP Repeat Responses", Nov. 16, 2015, pp. 1-18, London School of Hygiene and Tropical Medicine, United Kingdom.

Jennings et al., "The coming of age of virus-like particle vaccines", May 2008, pp. 521-536, vol. 389, Zurich-Schlieren, Switzerland.

Beernink et al., "A meningococcal factor H binding protein mutant that eliminates factor H binding enhances protective antibody responses to vaccination", Mar. 15, 2012, 186(6) pp. 3606-3614, PMC NIH Public Access.

"Thermo Scientific Crosslinking Technical Handbook", Life Science Research 2012.

Rogers et al., "Comparative Analysis of the Properties and Ligand Binding Characteristics of CspZ, a Factor H Binding Protein, Derived from Borrelia burgdorferi Isolates of Human Origin", Oct. 2009, p. 4396-4405, Infection and Immunity, Richmond, Virginia.

Coleman et al. "Borrelia burgdorferi Complement Regulator-Acquiring Surface Protein 2 Does Not Contribute to Complement Resistance of Host Infectivity", Aug. 20, 2008, vol. 3, Issue 8, pp. 1-9, Institute of Medical Research, Australia.

Marcinkiewicz et al., "Eliminating Factor H-Binding Activity of Borrelia burgdorferi CspZ Combined with Virus-Like Particle Conjugation Enhances Its Efficacy as a Lyme Disease Vaccine", Feb. 8, 2018, vol. 9, Article 181, Frontiers In Immunology, Italy.

Brangulis et al., "Structural characterization of CspZ, a complement regulator factor H and FHL-1 binding protein from Borrelia burgdorferi", Apr. 4, 2014, FEBS Journal, 281 pp. 2613-2622, Riga, Latvia.

Marcinkiewicz et al., "Blood-treatment of Lyme borreliae demonstrates the mechanism of CspZ-mediated complement evasion to promote systemic infection in vertebrate hosts", Dec. 20, 2018, pp. 1-59, Cellular Microbiology, Albany, New York.

(Continued)

*Primary Examiner* — Jennifer E Graser
(74) *Attorney, Agent, or Firm* — HESLIN ROTHENBERG FARLEY & MESITI

(57) ABSTRACT

Provided is an immunogenic composition including a peptide, wherein consecutive amino acids of the peptide include at least amino acids 186-193 of SEQ ID NO:1 and one or more adjuvants. In an example, the peptide is covalently linked to an amino acid sequence including SEQ ID NO:2. Also provided is a method of vaccinating a subject against *Borrelia burgdorferi*, including administering to the subject an effective amount of the immunogenic composition.

23 Claims, 12 Drawing Sheets

Specification includes a Sequence Listing.

(56) References Cited

OTHER PUBLICATIONS

Fraser et al "Genomic sequence of a Lyme disease spirochaete, Borrelia burgdorferi", Dec. 11, 1997, Nature 390, pp. 580-586.
Kraiczy et al. "Borrelia burgdorferi Complement Regulator-Acquiring Surface Protein 2 (CspZ) as a Serological Marker of Human Lyme Disease", Mar. 2008, Clin. Vaccine. Immunol. 15: 484-491.

COMPOSITION AND METHOD FOR GENERATING IMMUNITY TO *BORRELIA BURGDORFERI*

CROSS-REFERENCE TO RELATED APPLICATIONS

This application is a continuation of U.S. patent application Ser. No. 16/891,147, filed on Jun. 3, 2020, which is a continuation of U.S. patent application Ser. No. 16/229,452, filed on Dec. 21, 2018, and claims benefit of priority from U.S. Provisional Patent Application No. 62/611,212, filed Dec. 28, 2017, the entire contents of which applications are incorporated herein by reference in their entireties.

SEQUENCE LISTING

The instant application contains a Sequence Listing, created on Feb. 28, 2022; the file, in ASCII format, is designated H1361163H2277379.txt and is 4.0 KB in size. The file is hereby incorporated by reference in its entirety into the instant application.

FIELD OF THE INVENTION

The subject matter disclosed herein relates to compositions and methods for protecting against infection by *Borrelia burgdorferi*. More particularly, this disclosure relates to an immunogen and vaccine for generating immunity to *Borrelia burgdorferi*, including a vaccine for Lyme disease.

BACKGROUND OF THE INVENTION

Lyme disease is the most common vector-borne illness in North America and Europe. However, no vaccine is currently available for humans. In North America, Lyme disease is caused by the spirochete *Borrelia burgdorferi* sensu stricto (hereafter *B. burgdorferi*), which may be transmitted via *Ixodes* ticks. Upon tick feeding, spirochetes migrate from the ticks to the vertebrate hosts and infect the skin at the biting site, often resulting in an inflammatory skin lesion, called erythema migrans. If untreated, spirochetes disseminate via bloodstream to organs, causing disease manifestations including arthritis, carditis, and neuroborreliosis. To disseminate to distal tissues, *B. burgdorferi* needs to evade the complement system, an important host innate immune defense mechanism in the blood of vertebrate animals. Activation of the complement system results in the formation of C3 convertases, leading to the release of pro-inflammatory peptides, and pathogen opsonization and lysis. To avoid self-damage in the absence of pathogens, vertebrate animals produce complement inhibitors such as Factor H (FH) and FH-like protein 1 (FHL-1, the spliced form of FH). FH and FHL-1 bind to C3b, a component of C3 convertases, which recruits complement protein factor I to degrade C3b and inhibit the formation of these convertases and inactivates the complement system.

*B. burgdorferi* produces at least 5 distinct Complement Regulator Acquiring Surface Proteins including CspZ (CRASP-2). CspZ binds to human and mouse FH/FHL-1 to confer serum resistance in a gain-of-function *B. burgdorferi* by inhibiting complement activation on the spirochete surface. A cspZ deletion mutant of *B. burgdorferi* colonizes tissues at similar levels as its parental wild type strain, potentially due to the low production levels of CspZ when spirochetes are cultivated in vitro (Coleman A S, Yang X, Kumar M, Zhang X, Promnares K, et al. (2008) *Borrelia burgdorferi* Complement Regulator-Acquiring Surface Protein 2 Does Not Contribute to Complement Resistance or Host Infectivity. PLoS ONE 3(8): 3010e. doi:10.1371/journal.pone.0003010). Incubating wild type *B. burgdorferi* with human blood to induce the production of CspZ indicates that the wild type spirochete displays greater levels of bacteremia and dissemination in mice compared to a cspZ deletion mutant under the blood treatment condition (Marcinkiewicz et al., 2018, Blood-treatment of Lyme borreliae demonstrates the mechanism of CspZ-mediated complement evasion to promote systemic infection in vertebrate hosts, Cellular Microbiology, https://doi.org/10.1111/cmi.12998. These findings suggest that CspZ allows spirochete to survive in the blood and disseminate to different tissues during infection. cspZ expression is detectable when spirochetes are in mammalian hosts and in vitro cultivation, and inoculating mice with CspZ triggers antibody response against this protein. Although whether or not all isolates from Lyme disease borreliae species encode cspZ is still unclear, the isolates from *B. burgdorferi* (North American species of Lyme disease spirochetes) and the European Lyme disease borreliae strains that cause severe systemic infection all carry this gene (Rogers et al., 2007). The cspZ alleles among these Lyme borreliae isolates were grouped into three types and share more than 70% of sequence identity (Rogers et al., 2009; Rogers et al., 2007). These observations suggest that CspZ may have vaccinogenic potential by inducing antibody-mediated bactericidal activity against *B. burgdorferi*.

However, immunization with CspZ does not protect mice from infection (Coleman et al., 2008), raising a possibility that CspZ as a vaccine does not induce antibody titers robust enough to kill *B. burgdorferi*. The present disclosure is directed to overcoming these and other deficiencies in conventional technologies.

SUMMARY OF THE INVENTION

In an aspect, disclosed is an immunogenic composition including a peptide, wherein consecutive amino acids of the peptide include consecutive amino acids of SEQ ID NO:1 and the consecutive amino acids of SEQ ID NO:1 are selected from amino acids 186-193 of SEQ ID NO:1, 187-194 of SEQ ID NO:1, 188-195 of SEQ ID NO:1, 189-196 of SEQ ID NO:1, and any combination of two or more of the foregoing, and one or more adjuvants. In an embodiment, the consecutive amino acids of SEQ ID NO:1 are selected from amino acids 186-218 of SEQ ID NO:1, 187-218 of SEQ ID NO:1, 188-218 of SEQ ID NO:1, 189-218 of SEQ ID NO:1, and any combination of two or more of the foregoing. In another embodiment, the consecutive amino acids of SEQ ID NO:1 are selected from amino acids 1-193 of SEQ ID NO:1, 1-194 of SEQ ID NO:1, 1-195 of SEQ ID NO:1, 1-196 of SEQ ID NO:1, and any combination of two or more of the foregoing. In yet another embodiment, the consecutive amino acids of SEQ ID NO:1 are selected from amino acids 186-222 of SEQ ID NO:1, 187-222 of SEQ ID NO:1, 188-222 of SEQ ID NO:1, 189-222 of SEQ ID NO:1, and any combination of two or more of the foregoing. In a further embodiment, the peptide includes amino acids 1-218 of SEQ ID NO:1. In a still further embodiment, the peptide includes SEQ ID NO:1.

In another embodiment, the peptide is covalently linked to an amino acid sequence including SEQ ID NO:2. In yet another embodiment, a C-terminal amino acid of the peptide is covalently linked to an amino acid sequence comprising SEQ ID NO:2. In still another embodiment, the immunogenic composition further includes a covalent cross-link between the peptide and an amino acid sequence including SEQ ID NO:2, wherein the cross-link includes a thioether bond to the amino acid of the peptide corresponding to amino acid 222 of SEQ ID NO:1 and an amine linkage to a lysine amino acid of SEQ ID NO:2.

In a further embodiment, at least one of the one or more adjuvants includes aluminum salt, AS04, AS03, monophosphoryl lipid A, poly(I:C), a CpG DNA adjuvant, MF59, an emulsion adjuvant comprising squalene and water, a combination adjuvant comprising block copolymer CRL-8300, squalene, and a sorbitan monooleateor, N-[1-(2,3-Dioleoyloxy)propyl]-N,N,N-trimethylammonium salt (DOTAP), 3β-[N—(N',N'-dimethylaminoethane)-carbamoyl] cholesterol (DC-chol liposome), or SEQ ID NO:2.

In another aspect, provided is a method of vaccinating a subject against *Borrelia burgdorferi*, including administering to the subject an effective amount of an immunogenic composition including a peptide and one or more adjuvants, wherein consecutive amino acids of the peptide include consecutive amino acids of SEQ ID NO:1 and the consecutive amino acids of SEQ ID NO:1 are selected from amino acids 186-193 of SEQ ID NO:1, 187-194 of SEQ ID NO:1, 188-195 of SEQ ID NO:1, 189-196 of SEQ ID NO:1, and any combination of two or more of the foregoing. In an embodiment, the consecutive amino acids of SEQ ID NO:1 are selected from amino acids 186-218 of SEQ ID NO:1, 187-218 of SEQ ID NO:1, 188-218 of SEQ ID NO:1, 189-218 of SEQ ID NO:1, and any combination of two or more of the foregoing. In another embodiment, the consecutive amino acids of SEQ ID NO:1 are selected from amino acids 1-193 of SEQ ID NO:1, 1-194 of SEQ ID NO:1, 1-195 of SEQ ID NO:1, 1-196 of SEQ ID NO:1, and any combination of two or more of the foregoing. In yet another embodiment, the consecutive amino acids of SEQ ID NO:1 are selected from amino acids 186-222 of SEQ ID NO:1, 187-222 of SEQ ID NO:1, 188-222 of SEQ ID NO:1, 189-222 of SEQ ID NO:1, and any combination of two or more of the foregoing. In still another embodiment, the peptide includes amino acids 1-218 of SEQ ID NO:1. In a further embodiment, the peptide comprises SEQ ID NO:1.

In another embodiment, the peptide is covalently linked to an amino acid sequence including SEQ ID NO:2. In yet another embodiment, a C-terminal amino acid of the peptide is covalently linked to an amino acid sequence comprising SEQ ID NO:2. In still another embodiment, the immunogenic composition further includes a covalent cross-link between the peptide and an amino acid sequence comprising SEQ ID NO:2, wherein the cross-link includes a thioether bond to the amino acid of the peptide corresponding to amino acid 222 of SEQ ID NO:1 and an amine linkage to a lysine amino acid of SEQ ID NO:2.

In a further embodiment, at least one of the one or more adjuvants includes aluminum salt, AS04, AS03, monophosphoryl lipid A, poly(I:C), a CpG DNA adjuvant, MF59, an emulsion adjuvant comprising squalene and water, a combination adjuvant comprising block copolymer CRL-8300, squalene, and a sorbitan monooleateor, N-[1-(2,3-Dioleoyloxy)propyl]-N,N,N-trimethylammonium salt (DOTAP), 3β-[N—(N',N'-dimethylaminoethane)-carbamoyl] cholesterol (DC-chol liposome), or SEQ ID NO:2.

BRIEF DESCRIPTION OF THE DRAWINGS

These and other features, aspects, and advantages of the present disclosure will become better understood when the following detailed description is read with reference to the accompanying drawings, wherein:

FIG. 3A shows an example of an immunogenic composition in accordance with some embodiments disclosed herein. Purified wild-type CspZ or CspZ-YA with an exposed a sulphydryl group and virus-like particles ("VLP") generated from Qβ phage were mixed with Succinimidyl 6-((beta-maleimidopropionamido)hexanoate) ("SMPH") to crosslink VLP and each of these CspZ proteins ("VLP-CspZ").

FIG. 3B shows western blots of some examples of immunogenic compositions as disclosed herein. The sizes and purity of each conjugate were determined by a 15% SDS-PAGE. The molecular marker (kD) is in lane 1, followed by preparations of VLP (lane 2), CspZ (lane 3), VLP-CspZ (lane 4), and VLP-CspZ-YA (lane 5). The arrows identify known protein products as indicated.

FIG. 5A and FIG. 5B show that serum from mice immunized i.p. with VLP-CspZ-YA had more robust levels of bactericidal activity than VLP- or VLP-CspZ-vaccinated mice. Serum collected C3H/HeN mice at 42 days post inoculation of PBS, VLP, CspZ, VLP-CspZ, or VLP-CspZ-YA were mixed at indicated dilutions with guinea pig complement and $5\times10^5$ cells/mL *B. burgdorferi* strain B31-

A3. Surviving spirochetes were quantified using dark-field microscopy after 24 hours of incubation. FIG. 5A. The survival percentage was derived from the proportion of serum-treated to untreated *B. burgdorferi*. FIG. 5B. The 50% borreliacidal titer of each serum sample, representing the dilution rate of the serum that effectively killed 50% of spirochetes, was plotted. Data shown are the mean±standard error of the mean, of three (PBS) or five (all others) mice per group. Statistical significance (p<0.05) of differences in bactericidal titers relative to PBS-inoculated mice were determined using a t-test and are indicated ("*").

FIGS. 11A and 11B are graphs demonstrating that serum from mice immunized with VLP-CspZ-YA had more robust levels of bactericidal activity than CspZ-YA-vaccinated mice. Serum collected five C3H/HeN mice at 42 days post inoculation i.d. of PBS, CspZ-YA, or VLP-CspZ-YA was mixed at indicated dilutions with guinea pig complement and $5 \times 10^5$ cells/mL *B. burgdorferi* strain B31-A3. The serum collected from four unvaccinated C3H/HeN mice was included as negative control ("NMS", normal mouse serum). Surviving spirochetes were quantified using dark-field microscopy after 24-hours of incubation. In FIG. 11A, survival percentage was derived from the proportion of serum-treated to untreated *B. burgdorferi*. Data shown are the mean±standard error of the mean of survival percentage derived from three fields under the microscope for each sample. In FIG. 11B, the 50% borreliacidal titer of each serum sample, representing the dilution rate of the serum that effectively killed 50% of spirochetes, was obtained from the cure-fitting in FIG. 11A. Data shown are the mean±standard error of the mean of borreliacidal titers of each serum sample derived from five CspZ, VLP-CspZ, or VLP-CspZ-YA mice per group (also see Table 4). The 50% borreliacidal titers of the serum samples from PBS- or VLP-inoculated mice were not detectable ("NK", No killing) as those serum samples displayed no bactericidal activity. Statistical significances (p<0.05) of differences in bactericidal titers relative to CspZ-YA-immunized mice were determined using a t-test and are indicated ("*").

FIGS. 13A and 13B show that either CspZ-YA or VLP-CspZ-YA immunization prevents Lyme arthritis in *B. burg-*

*dorferi*-infected C3H/HeN mice at levels similar to uninfected mice. Five C3H/HeN mice were inoculated i.d. with PBS, CspZ-YA, or VLP-CspZ-YA and subsequently fed by nymphs carrying *B. burgdorferi* strain B31-A3. Tibiotarsus joints were collected 21 days post feeding, and also from five PBS-inoculated five mice fed by uninfected nymphs ("PBS", uninfected mice). To assess inflammation, tissues were fixed and stained with hematoxylin and eosin. FIG. 13A. The representative images from one mouse per group are shown here. Top panels are lower-resolution images (joint, ×10 [bar, 160 μm]); bottom panels are higher-resolution images (joint, 2×20 [bar, 80 μm]) of selected areas (insets in top panels). Arrows indicate infiltration of immune cells. FIG. 13B. To quantitate inflammation of joint tissues, at least ten random sections from each infection group were scored on a scale of 0-3 for the severity of arthritis, as indicated in Materials and Methods. Statistical significance was determined using a one-way ANOVA test. Data shown are the mean inflammation score±Standard deviation of 5 mice per group. Statistical significance was determined using a one-way ANOVA test. Asterisks ("*") indicate the significant (P<0.05) differences in the inflammation score relative to uninfected mice.

DETAILED DESCRIPTION OF THE INVENTION

Figure 1A:
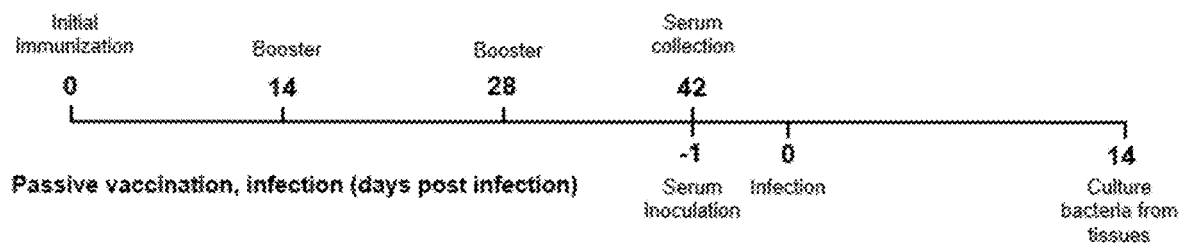
FIG. 1A shows an experimental timeline of passive immunization as disclosed herein. C3H/HeN mice received i.p. immunization and two boosters (14 and 28 days post immunization) of VLP, CspZ, VLP-CspZ, or VLP-CspZ-YA, or PBS. Fourteen days after the final booster, post-immunization serum was collected. Naive SW mice (six mice per group) were inoculated with serum from each group of the mice or pre-immune serum. Then, these mice were infected with $10^4$ *B. burgdorferi* strain B31-A3. Tissues collected at 14 days post infection were placed in culture medium to determine whether *B. burgdorferi* was present in the tissues.

This disclosure relates to a composition and method for generating immunity. In particular, disclosed is an immunogen including modified CspZ or portions of modified CspZ from *Borrelia burgdorferi*. In some examples, the immunogen also includes bacteriophage Qβ-derived VLP. The modified CspZ may be modified so as to not bind FH or to bind FH minimally, weakly, or transiently. Inoculation with a vaccine including such an immunogen induces antibodies that may efficiently eradicate spirochetes in vitro and prevents Lyme-associated arthritis and tissue colonization in vivo.

An immunogenic composition as disclosed herein may contain a polypeptide including amino acids of SEQ ID NO:1, or portions of SEQ ID NO:1. SEQ ID NO:1 is a portion of CspZ from *Borrelia burgdorferi*, with a serine residue at amino acid 1. Alanine amino acids at amino acid positions 189 and 193 of SEQ ID NO:1 are modified from CspZ of *Borrelia burgdorferi*, which naturally has tyrosines at these sites. Mutations of these sites has previously been shown to prevent CspZ from binding to FH.

An amino acid sequence of eight or more consecutive amino acids amino acids of a sequence of a portion of or full-length SEQ ID NO:1 may be used as an immunogenic composition as disclosed herein, such as a vaccine, provided that it includes amino acids 189 and 193 of SEQ ID NO:1 (or amino acid substitutions for tyrosine other than alanine at one or both of these positions). Examples include a peptide sequence including 8 or more consecutive amino acids corresponding to at least amino acids 186-193 of SEQ ID NO:1, 187-194 of SEQ ID NO:1, 188-195 of SEQ ID NO:1, 189-196 of SEQ ID NO:1, or any combination of two or more of the foregoing. Other examples include a peptide sequence including 8 or more consecutive amino acids corresponding to at least amino acids 186-218 of SEQ ID NO:1, 187-218 of SEQ ID NO:1, 188-218 of SEQ ID NO:1, 189-218 of SEQ ID NO:1, or any combination of two or more of the foregoing. Other examples include a peptide sequence including 8 or more consecutive amino acids corresponding to at least amino acids 1-193 of SEQ ID NO:1, 1-194 of SEQ ID NO:1, 1-195 of SEQ ID NO:1, 1-196 of SEQ ID NO:1, or any combination of two or more of the foregoing. Other examples include a peptide sequence including 8 or more consecutive amino acids corresponding to at least amino acids 186-222 of SEQ ID NO:1, 187-222 of SEQ ID NO:1, 188-222 of SEQ ID NO:1, 189-222 of SEQ ID NO:1, or any combination of two or more of the foregoing. Other examples include amino acids 1-218 of SEQ ID NO:1 and amino acids 1-222 of SEQ ID NO:1.

Other examples include amino acids 2-193 of SEQ ID NO:1, amino acids 2-196 of SEQ ID NO:1, amino acids 180-222 of SEQ ID NO:1, amino acids 170-222 of SEQ ID NO:1, amino acids 160-222 of SEQ ID NO:1, amino acids 150-222 of SEQ ID NO:1, amino acids 140-222 of SEQ ID NO:1, amino acids 130-222 of SEQ ID NO:1, amino acids 120-222 of SEQ ID NO:1, amino acids 110-222 of SEQ ID NO:1, amino acids 100-222 of SEQ ID NO:1, amino acids 90-222 of SEQ ID NO:1, amino acids 80-222 of SEQ ID NO:1, amino acids 70-222 of SEQ ID NO:1, amino acids 60-222 of SEQ ID NO:1, amino acids 50-222 of SEQ ID NO:1, amino acids 40-222 of SEQ ID NO:1, amino acids 30-222 of SEQ ID NO:1, amino acids 20-222 of SEQ ID NO:1, amino acids 10-222 of SEQ ID NO:1, and amino acids 2-222 of SEQ ID NO:1.

In some examples, the immunogenic composition may include consecutive amino acids of SEQ ID NO:1 other than amino acids corresponding to 8 or more consecutive amino acids spanning from amino acids 186-196 of SEQ ID NO:1. In some examples, such amino acids may have 100% homology to those of SEQ ID NO:1 other than amino acids corresponding to 8 or more consecutive amino acids spanning from amino acids 186-196 of SEQ ID NO:1. Or, they may have less than 100% homology. For example, they may have at least 99% homology, or at least 95% homology, or at least 90% homology, or at least 85% homology, or at least 80% homology, or at least 75% homology, or at least 70% homology to consecutive amino acids of SEQ ID NO:1 other than amino acids corresponding to 8 or more consecutive amino acids spanning from amino acids 186-196 of SEQ ID NO:1. That is, in some examples, an immunogenic composition as disclosed herein may vary in amino acid sequence from such regions of SEQ ID NO:1 other than amino acids corresponding to 8 or more consecutive amino acids spanning from amino acids 186-196 of SEQ ID NO:1.

In another embodiment, the at least 8 consecutive amino acids of SEQ ID NO:1 may be covalently linked to an amino acid of SEQ ID NO:2. Amino acids 219-222 of SEQ ID NO:1 may be a linking sequence, optionally present in some embodiments of an immunogenic composition as disclosed herein, optionally for linking an immunogenic composition of SEQ ID NO:1 or portion of 8 or more consecutive amino acids thereof to an amino acid of sequence of SEQ ID NO:2. In other examples, a different amino acid sequence may be used between consecutive amino acids corresponding to those of SEQ ID NO:1 and, optionally, a linker to an amino acid of SEQ ID NO:2, which linker is described in more detail below.

The polypeptide sequence of SEQ ID NO:2 is a sequence derived from a coat protein of bacteriophage Qβ. Polypeptides of a sequence of SEQ ID NO:2 may form a VLP and enhance immunogenicity of an immunogen with which it is co-administered to a subject. Immunogens may be covalently linked to amino acids of a sequence of SEQ ID NO:2. For example, linking agents well known to skilled artisans may be used to form covalent linkages to amine groups, such as side-chains of lysine residues. For example, a linking agent with a reactive group that can form a covalent linkage with an amine group, such as an N-hydroxysuccinimide ester, may be used to link another polypeptide to a lysine residue of an amino acid of a sequence of SEQ ID NO:2 (e.g., a lysine residue at amino acid 3, 14, 16, 47, 61, 64, or 68), by formation of an amide bond and release of N-hydroxysuccinimide. A modified peptide or other compound containing or modified to include an N-hydroxysuccinimide ester group may be brought into contact with a polypeptide having the amino acid sequence of SEQ ID NO:2 resulting in the formation of an amine linkage or linkages between the modified peptide or compound and the polypeptide having the amino acid sequence of SEQ ID NO:2. As would be appreciated by skilled artisans, other chemical groups that form linkages with amide groups, including an isothiocyanate, an isocyanate, a sulfonyl chloride, an aldehyde, a carbodiimide, an acyl azide, an anhydride, a fluorobenzeny, a carbonate, an imidoester, an epoxide, a flouorophenyl ester, or similarly reactive group, could be similarly used in place of N-hydroxysuccinimide to link a modified peptide or compound to a polypeptide having an amino acid sequence of SEQ ID NO:2, in accordance with the present disclosure.

In an example, a cysteine residue of the at least 8 consecutive amino acids of SEQ ID NO:1 may linked to a lysine reside of SEQ ID NO:2. In a further example, the cysteine residue may be a C-terminal residue. In another example, the at least 8 amino acids of SEQ ID NO:1 may be linked to the amino acids of SEQ ID NO:2 by a cross-linker. In an example, the cross-linker may include an amine linkage to SEQ ID NO:2, a thioether linkage to the at least 8 consecutive amino acids of SEQ ID NO:1 wherein at least 5 of the consecutive amino acids comprise amino acids 189-193 of SEQ ID NO:1, or both. Amino acids other than cysteine, or modified amino acids, capable of forming covalent attachment to different linkers may also be used. In some examples, an immunogenic amino acid sequence with consecutive amino acids corresponding to at least some of those of SEQ ID NO:1 may be non-covalently linked to amino acid sequences of SEQ ID NO:2.

An amino acid containing a cysteine residue, such as, for example, an amino acid of a portion of SEQ ID NO:1 that includes amino acid 222, may be covalently linked to an amino acid of sequence of SEQ ID NO:2. For example, linking agents well known to skilled artisans may be used to form covalent linkages to sulfhydryl residues, such as present in cysteine. For example, a linking agent with a reactive group that can form a covalent linkage with an amine group, such as a maleimide group, may be used to link another polypeptide to a cysteine residue of an amino acid of a sequence of SEQ ID NO:1 or portion thereof (e.g., a cysteine residue at position 222 of SEQ ID NO:1), by formation of a thioester bond. A modified peptide or other compound containing or modified to include amaleimide group may be brought into contact with a polypeptide having the amino acid sequence of SEQ ID NO:1 or portion thereof containing a sulfhydryl group such as a csyteine reside resulting in the formation of a thioester linkage or linkages between the modified peptide or compound and the polypeptide having the amino acid sequence of SEQ ID NO:1 or partial sequence thereof. As would be appreciated by skilled artisans, other chemical groups that form linkages with sulfhydryl groups, including a haloacetyl group or pyridyl disulfide group, could be similarly used in place of a maleimide group to link a modified peptide or compound to a polypeptide having an amino acid sequence of SEQ ID NO:1 or partial sequence thereof containing a sulfhydryl group, such as a cysteine, in accordance with the present disclosure.

A linker may contain both a reactive group that reacts with an amide group to form an amine linkage and a reactive group that reacts with a sulfhydryl group to form a thioester linkage, thereby covalently attaching a composition to which the linker is attached by an amine linkage to a composition to which the linker is covalently attached by a thioester linkage. A linker may contain a spacer arm spanning between the reactive functional groups, such as a $C_1$ to $C_{20}$ hydrocarbyl, oxaalkyl, thiaalkyl, or azaalkyl linkage. $C_1$ to $C_{20}$ hydrocarbyl (or any subset thereof, e.g. ($C_1$-$C_6$) hydrocarbyl), includes alkyl, alkenyl, alkynyl, aryl and combinations thereof. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

In an example, the vaccine further includes an adjuvant. In another embodiment, the subject may be a mammal. In another embodiment, the subject may be a human.

An adjuvant is a composition included with an immunogenic compound, such as in a vaccine, for enhancing an immunogenic response in a subject to which it is administered. Many adjuvants are known to skilled artisans and may be administered to a subject with an immunogenic composition as disclosed herein for the purpose of stimulating or promoting an immune response against *Borrelia burgdorferi*. Non-limiting examples of adjuvants that could be included in a vaccine with an immunogenic compound as disclosed herein include an aluminum salt, AS04, AS03, monophosphoryl lipid A, poly(I:C), a CpG DNA adjuvant, MF59 or other emulsion adjuvant, an emulsion adjuvant comprising squalene and water, a virosomal adjuvant, a cytokine, TITERMAX® Gold adjuvant (a combination adjuvant including block copolymer CRL-8300, squalene, and a sorbitan monooleateor), N-[1-(2,3-Dioleoyloxy)propyl]-N,N,N-trimethylammonium salt (DOTAP), 3β-[N—(N',N'-dimethylaminoethane)-carbamoyl] cholesterol (DC-chol liposome), SEQ ID NO:2, or a combination of any two or more of the foregoing. Including any one or more of the foregoing adjuvants together with an immunogenic composition as disclosed herein may promote development of an immunological response. Any one or more of the foregoing could be combined with any immunogenic composition in accordance with the present disclosure for creation of a vaccine or stimulating immunogenecity to Borrelia burgdorferi.

An immunogenic composition or vaccine as disclosed herein may be administered to a subject such as a mammal, including a rodent, dog, cat, human, cattle, cervid, or other mammal. Administration may be by subcutaneous, intradermal, intramuscular, intraperitoneal, intranasal, oral, or otherwise.

EXAMPLES

The following examples are intended to illustrate particular embodiments of the present disclosure, but are by no means intended to limit the scope thereof.

Materials and Methods

Mouse and bacterial strains. Three-week-old, male C3H/HeN and Swiss Webster mice were purchased from Charles River (Wilmington, Mass., USA) and Taconic (Hudson, N.Y., USA), respectively. The Borrelia burgdorferi strain B31-A3 used in this study is a clonal isolate of B31, and was grown at 33° C. in BSK II complete medium. Ixodes scapularis tick larvae were obtained from BEI Resources (Manassas, Va.). Cultures were tested with PCR to ensure a full plasmid profile prior to use. Escherichia coli strains DH5α, BL21(DE3), and derivatives were grown at 37° C. in Luria-Bertani (BD Bioscience, Franklin lakes, N.J.) broth or agar, supplemented with kanamycin (25 µg/mL), ampicillin (100 µg/mL), or no antibiotics when appropriate.

Generation of VLP-CspZ proteins. To produce recombinant glutathione-S-transferase (GST)-tagged CspZ proteins, the plasmid pGEX-6P1 encoding the open reading frames lacking the putative signal sequences of bbh06 (cspZ) from B. burgdorferi strains B31 (residue 20 to 236 of CspZ) or an altered open reading frame encoding CspZ-YA (residue 20 to 236 of CspZ with tyrosine-207 and -211 (corresponding to amino acids 189 and 193, respectively, of SEQ ID NO:1) replaced by alanine) generated previously (Hartmann et al., 2006; Siegel et al., 2008) was transformed into E. coli strain BL21(DE3). The GST-tagged CspZ or CspZ-YA were produced and purified by GST affinity chromatography as described previously according to the manufacturer's instructions (GE Healthcare, Pittsburgh, Pa.). To produce recombinant CspZ proteins without affinity tags for VLP conjugation and vaccination, a cysteine has been added to C-termini of both CspZ and CspZ-YA for coupling these proteins to VLPs. The genes encoding these proteins were cloned into the pETm_11 expression vector (EMBL) encoding an N-terminal 6×His-tag followed by a TEV protease cleavage site, resulting in an amino acid sequence of MHHHHHHENLYFQS-CspZ-GSGC (MHHHHHHEN-LYFQS: SEQ ID NO:3). E. coli XL1-Blue cells were transformed with the plasmids encoding cspZ or cspZ-YA.

The transformations were verified by sequencing the plasmid DNA extracted from isolated colonies. E. coli BL21 (DE3) cells were transformed with these plasmids and grown in modified 2×TY medium at 37° C. until mid-log phase. The cultures were then induced to produce CspZ with 0.2 mM isopropyl thio-β-D-galactoside, and grown overnight at 20° C. The cells were lysed by sonication. After removing the debris, the supernatant was loaded onto a HisTrap FF column (GE Healthcare, Chicago, Ill.) and eluted with 300 mM imidazole at pH 7.5. The 6×His tag was removed by incubation with TEV protease at 4° C. overnight. Imidazole was removed by dialyzing the proteins in PBS buffer. The protease, the digested 6×His tag, and un-cleaved proteins were removed using an additional round of HisTrap FF column purification. The purified protein fraction was concentrated using an Amicon centrifugal filter unit (Millipore, Billerica, Mass.). The purity of the recombinant proteins was evaluated by SDS-PAGE. The bacteriophage Qβ-derived VLPs were generated as previously described (Kozlovska et al., 1993). Purified CspZ proteins were chemically conjugated to VLPs with SMPH (Succinimidyl-6-[(β-maleimidopropionamido) hexanoate]) following the manufacturer's protocol (ThermoFisher, Waltham, Mass.). The unbounded protein was removed using a Superdex200 size exclusion column (GE Healthcare).

FH binding assays by ELISA. Quantitative ELISA for mouse FH binding by CspZ proteins was performed. Basically, one µg of BSA (negative control) or FH from mouse (MyBiosource, San Diego, Calif.) was coated onto microtiter plate wells. One hundred microliters of increasing concentrations (0.03125, 0.0625, 0.125, 0.25, 0.5, 1, 2 µM) of GST (negative control) or a GST tagged wild type or mutant CspZ protein, including CspZ or CspZ-YA were then added to the wells. To detect the binding of GST-tagged proteins, mouse anti-GST tag (Sigma-Aldrich, St. Louis, Mo.; 1:200) and HRP-conjugated goat anti-mouse IgG (Promega, Madison, Wis.; 1:1,000×) were used as primary and secondary antibodies. The plates were washed three times with PBST (0.05% Tween 20 in PBS), and 100 µL of tetramethyl benzidine (TMB) solution (ThermoFisher) were added to each well and incubated for five minutes. The reaction was stopped by adding 100 µL of 0.5% hydro sulfuric acid to each well. Plates were read at 405 nm using a Tecan Sunrise Microplate reader (Tecan, Morrisville, N.C.).

Figure 1B:
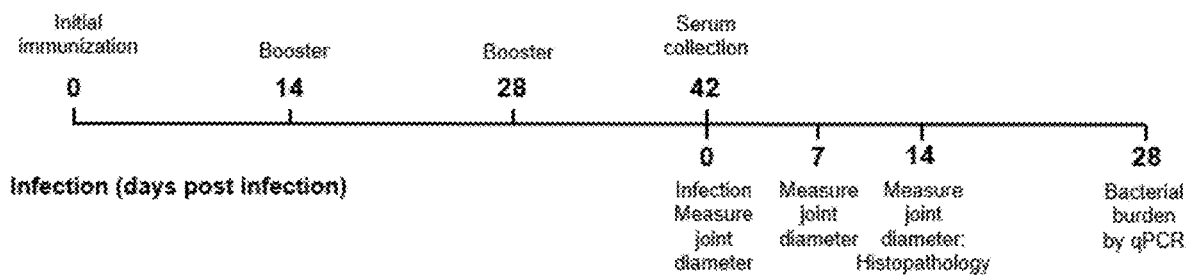
FIG. 1B shows an experimental timeline of active immunization as disclosed herein. C3H/HeN mice received i.p. immunization and two boosters (14 and 28 days post immunization) of VLP, CspZ, VLP-CspZ, or VLP-CspZ-YA, or PBS. Fourteen days after the final booster, post-immunization serum was collected, and mice were infected with $10^4$ *B. burgdorferi* strain B31-A3. The diameter of the tibiotarsus joints were measured prior to infection as well as 7 and 14 days post infection. Mice were sacrificed 14 days post infection for histopathology, or 28 days post infection for bacterial burden quantification.
Figure 9:
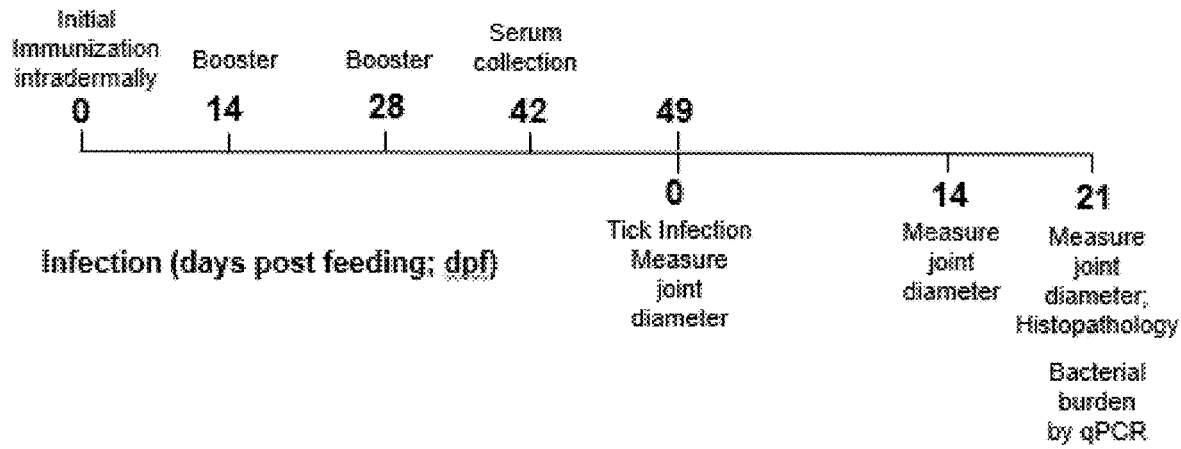
FIG. 9 depicts experimental timeline of mouse immunization and infection. C3H/HeN mice received i.d. immunization and two boosters (14 and 28 days post immunization) of CspZ-YA, VLP-CspZ-YA, or PBS. Forty-two days after the initial immunization, sera from these mice were collected to detect IgG or IgM titers and bactericidal activity. Forty-nine days after initial immunization, uninfected or *B. burgdorferi* strain B31-infected nymphal ticks were placed on those mice. The diameter of the tibiotarsus joints were measured prior to infection as well as 0, 14 and 21 days post tick feeding. Mice were sacrificed 21 days post infection for histopathology and bacterial burden quantification.

Mouse immunization. Twenty-five micrograms of VLP, CspZ, VLP-CspZ, CspZ-YA or VLP-CspZ-YA were thoroughly mixed with 504, TITERMAX® Gold adjuvant (a combination adjuvant including block copolymer CRL-8300, squalene, and a sorbitan monooleateor) (Norcross, Ga. USA) then inoculated into C3H/HeN mice intraperitoneally (i.p.) or intradermally (i.d.). Mice inoculated with 100 µL PBS were included as negative control mice. Mice received boosters of the same composition at 14 and 28 days post immunization, for a total of three immunizations over six weeks. FIGS. 1A, 1B, and 9.

Quantification of anti-CspZ titers with ELISA. Forty-two days post immunization, 100 µL blood was collected from the mice via submandibular bleeding to isolate serum. The sera were used to determine the titers of immunoglobulin M or G against CspZ using kinetic ELISA. In brief, microtiter plate wells were coated with 1 µg of recombinant CspZ. After blocking with 5% BSA (Sigma-Aldrich) in phosphate-buffered saline, 50 µL of mouse serum diluted 1:100, 1:300, 1:900, 1:1800, 1:3600, 1:7200, 1:144,000, or 1:288,000 was added to each well. HRP-conjugated goat anti-mouse IgM or IgG (1:20,000; Bethyl, Montgomery, Tex., USA) was then added into the wells, and the binding was detected at 620 nm for 10 cycles of 60 second kinetic intervals with 10 seconds shaking duration in a Sunrise absorbance ELISA plate reader (Tecan, Mannedorf, Switzerland). The greatest maximum slope of optical density/minute per sample was multiplied by the respective serum dilution factor to indicate the antibody titers (arbitrary Unit (A.U.)).

B. burgdorferi bactericidal activity of serum from immunized mice. Forty-two days post immunization, 100 μL blood was collected from the mice via submandibular bleeding to isolate serum. The mouse sera were used to determine the bactericidal activity against B. burgdorferi with serum bactericidal assays modified from previous studies. Before determining the bactericidal activity, these mouse sera were heat treated at 56° C. for 30 minutes to inactivate the complement system in these sera. Then, 50 μL of diluted mouse serum (1:20, 1:40, 1:80, 1:160, 1:320, 1:640, 1:1280, and 1:2560) was mixed with 10 μL of complement preserved guinea pig serum (guinea pig complement, Sigma-Aldrich, #S1639) or heat-inactivated guinea pig serum (negative control) as well as B. burgdorferi strain B31-A3 ($5 \times 10^5$ cells/mL) in 40 μL of BSK II complete medium and then incubated at 33° C. for 24 hours. Surviving spirochetes were quantified by directly counting only motile spirochetes using dark-field microscopy. The survival percentage was the proportion of serum-treated to untreated B. burgdorferi. The 50% borreliacidal titer representing the serum dilution rate that effectively killed 50% of spirochetes was calculated using dose-response stimulation fitting in GraphPad Prism 5.04 (GraphPad Software, La Jolla, Calif., USA).

Passive immunization of mice. Naive Swiss Webster mice were intraperitoneally inoculated with 100 μL of pooled serum from VLP-, CspZ-, VLP-CspZ-, or VLP-CspZ-YA-immunized mice. FIG. 1A. Mice inoculated with pre-immune serum were included as negative control. They were then challenged subcutaneously with $10^4$ infectious B. burgdorferi strain B31-A3 the next day. Mice were euthanized at 14 days post infection, and the inoculation site of skin, heart, tibiotarsus joints, bladder, and ears were collected and then placed at 33° C. in BSK medium supplemented with antimicrobial agents (rifampin at 50 mg/mL, phosphomycin at 200 mg/mL, and amphotericin B at 8 mg/mL). Cultures were checked weekly for four weeks using dark-field microscopy to determine whether the live B. burgdorferi was present. A mouse was considered infected when at least one culture was positive.

Active immunization of mice and tibiotarsus joint measurement. Forty-two days post immunization, the diameter of both tibiotarsus joints were measured with Digimax calipers (Bel-Art, Wayne, N.J., USA). Mice were then subcutaneously needle-infected with $10^4$ B. burgdorferi strain B31-A3 suspended in 100 μL BSK II incomplete medium. FIG. 1B. Negative control mice were injected with an equal volume of BSK II incomplete medium. The diameter of both tibiotarsus joints were measured prior to infection and then were re-measured 7 and 14 days post infection, and the diameters from each mouse averaged as Lyme-induced joint swelling is detectable as early as these time points.

Mouse infection experiments by ticks and tibiotarsus joint measurement for comparison of CspZ-YA and VLP-CspZ-YA as immunogens. Four-week-old male and female C3H/HeN mice were infected with $10^5$ of B. burgdorferi strain B31-A3 by intradermal injection as described above. The ear punches from those mice were collected and placed into BSKII medium at 7 days post infection, and the spirochete growth in the medium was evaluated to confirm the infection of these mice. At 14 days post infection, the uninfected larvae were allowed to feed to repletion on those B. burgdorferi-infected C3H/HeN mice. Approximately 100 to 200 larvae were allowed to feed on each mouse. The engorged larvae were collected and allowed to molt into nymphs in 4 to 6 weeks in a desiccator at room temperature and 95% relative humidity in a room with light dark control (light to dark, 12:12 hours). At 49 days post immunization, the flat nymphs molted from larvae were placed in a chamber on four to six-week old male and female C3H/HeN mice previously inoculated with PBS, CspZ-YA, or VLP-CspZ-YA (FIG. 9). Additional group of mice previously inoculated with PBS will be fed by uninfected nymphs as negative control. Ten nymphs were allowed to feed on each mouse. The nymphs were allowed to feed to repletion. Prior to tick feeding, the diameter of both tibiotarsus joints were measured with Digimax calipers (Bel-Art, Wayne, N.J., USA). The diameter of both tibiotarsus joints were re-measured at 14 and 21 days post feeding, and the diameters from each mouse averaged as Lyme-induced joint swelling is detectable as early as these time points.

Histopathology of B. burgdorferi infected mice. Mice were sacrificed 14 days post infection to assess arthritis and carditis or, for experiments comparing CspZ-YA to VLP-CspZ-YA, 21 days post tick feeding to assess arthritis. Thus, tibiotarsus joints were collected for tissue histopathology. Tissues were fixed for 48 hours in 10% neutral-buffered formalin, and subsequently decalcified for one week in 10% formic acid. Fixed tissues were prepared as slides stained with hematoxylin and eosin. Sections were evaluated for signs of arthritis using histological parameters for B. burgdorferi-induced inflammation, such as exudation of inflammatory cells into joints, altered thickness of tendons or ligament sheaths, and hypertrophy of the synovium. Inflammation was scored as 0 (no inflammation), 1 (mild inflammation with less than two small foci of infiltration), 2 (moderate inflammation with two or more foci of infiltration), or 3 (severe inflammation with focal and diffuse infiltration covering a large area). Arthritis were evaluated in a blind fashion as described previously (Lin et al., 2014).

Quantification of B. burgdorferi burden in infected mouse tissue with qPCR. To quantify B. burgdorferi bacterial burden, mice were sacrificed at 28 days post infection and inoculation site of the skin, knees, and hearts were collected. DNA was purified from tissues using either DNeasy Blood and Tissue Kit (Qiagen, Valencia, Calif.) or EZ-10 Spin Column Animal Genomic DNA Mini-Prep Kit (Bio Basic, Inc., Markham, Ontario, Calif.). The quantity and quality of DNA were assessed by measuring the concentration of DNA and the ratio of the UV absorption at 280 nm to 260 nm using a Nanodrop 1000 UV/Vis spectrophotometer (Thermo Fisher Scientific, Waltham, Mass., USA). Quantitative PCR (qPCR) was then performed to quantitate B. burgdorferi burden, as described previously (Lin et al., 2014). In brief, B. burgdorferi genomic equivalents were calculated using an Applied Biosystems 7500 Real-Time PCR system (Thermo Fisher Scientific, Waltham, Mass., USA) in conjunction with PowerUp™ SYBR® Green Master Mix (Thermo Fisher Scientific, Waltham, Mass., USA), based on amplification of the B. burgdorferi recA gene using primers BBRecAfp (5'-GTGGATCTATTGTATTAGATGAGGCTCTCG-3') (SEQ ID NO:4) BBRecArp (5'-GCCAAAGTTCTGCAACATTAACACCTAAAG-3') (SEQ ID NO:5). Cycling parameters were 50° C. for 2 minutes, 95° C. for 10 minutes, and 45 cycles of 95° C. for 15 seconds and 60° C. for 1 minute. The number of recA copies was calculated by establishing a threshold cycle (Ct) standard curve of a known number of recA gene extracted from B31-A3, and burdens were normalized to 10 ng of total DNA.

Statistical analyses. Significant differences between groups were determined with one-tailed Fisher Exact Probability Test or one-way ANOVA and post-hoc tests (GraphPad Software, La Jolla, Calif., USA). A p-value<0.05 was used to determine significance.

Results

Figure 2:
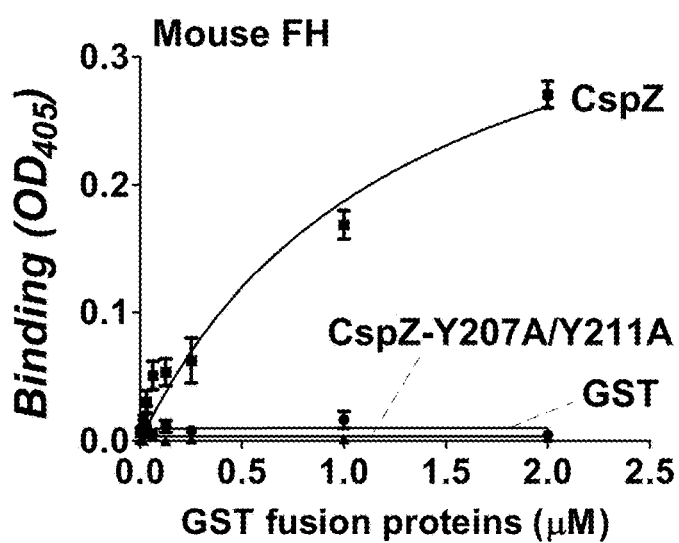
FIG. 2 is a graph demonstrating that recombinant version of CspZ-YA is incapable of binding to mouse FH. The indicated concentrations of GST tagged CspZ ("CspZ") or CspZ-YA ("CspZ-YA") or GST were added to triplicate wells coated with 1 μg of BSA (negative control, data not shown) or mouse FH, and protein binding was quantitated by ELISA. Numbers represent the mean±standard deviation. Data represent the average of four replicates.
Figures 3A, 3B:
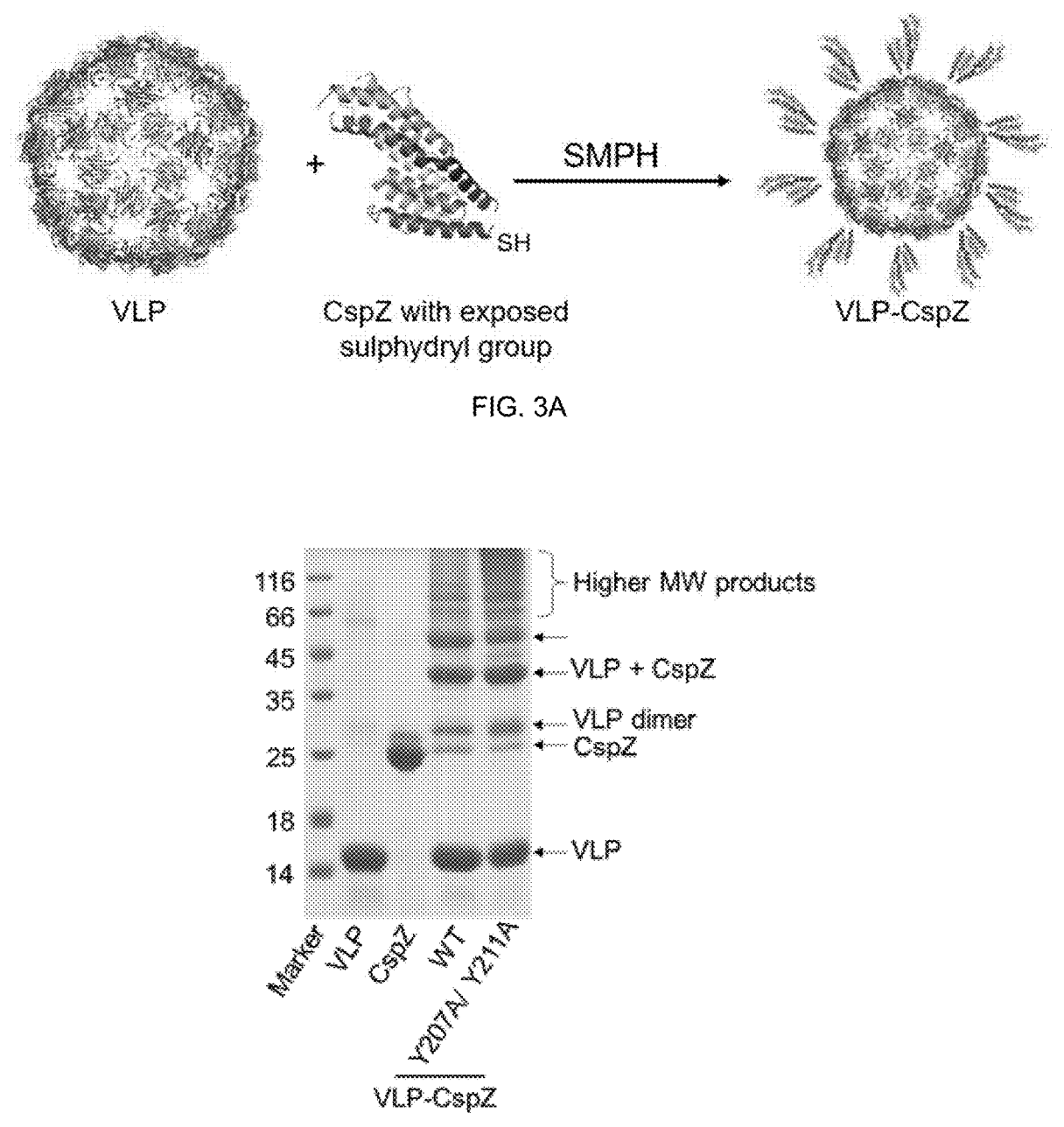
Figure 3C:
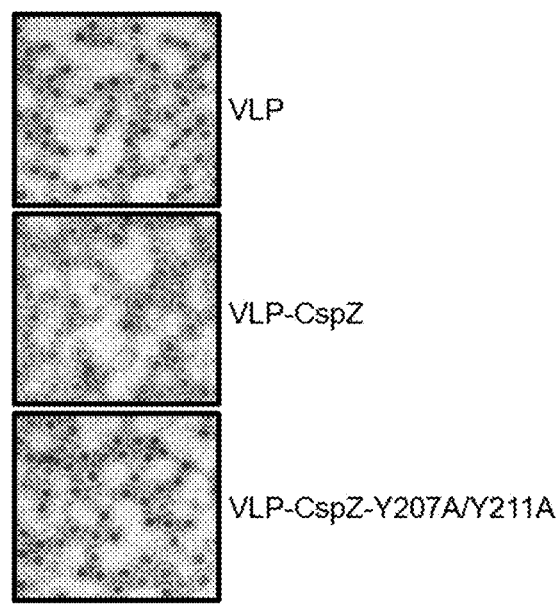
FIG. 3C shows electron micrographs of some examples of immunogenic compositions disclosed herein.

The generation and verification of VLP-conjugated CspZ proteins. The potential of CspZ as a vaccine was evaluated by using two different strategies: conjugating CspZ with VLP ("VLP-CspZ") and further modifying CspZ to eliminate its FH-binding activity ("VLP-CspZ-YA"). The point mutant CspZ-YA has been shown with no human FH-binding activity (Siegel et al., 2008). Because murine model of Lyme disease infection was used in this study to test the vaccine efficacy of these CspZ-derived proteins, the mouse FH-binding activity of CspZ-YA was measured by quantitative ELISA. As shown in FIG. 2, CspZ binds to mouse FH in a dose dependent manner whereas CspZ-YA does not bind to mouse FH. Regarding to the conjugation of VLP, the VLP utilized in this study was derived from the RNA bacteriophage Qβ, which is used extensively in vaccine development (Ambuhl et al., 2007; Bachmann and Jennings, 2011; Wiessner et al., 2011; Beeh et al., 2013). Recombinant CspZ proteins were attached to VLPs by adding an engineered C-terminal cysteine to CspZ and linking it to surface-exposed lysine amino groups of VLPs using SMPH (Succinimidyl 6-((beta-maleimidopropionamido)hexanoate)) cross-linker (FIG. 3A). The efficiency of coupling and was verified by SDS-PAGE. Similar to other VLP-conjugated proteins (Spohn et al., 2010), oligomerized coat protein of VLP was observed on SDS-PAGE (FIG. 3B). VLP integrity was maintained as observed under electro-microscopy (FIG. 3C).

Figure 4:
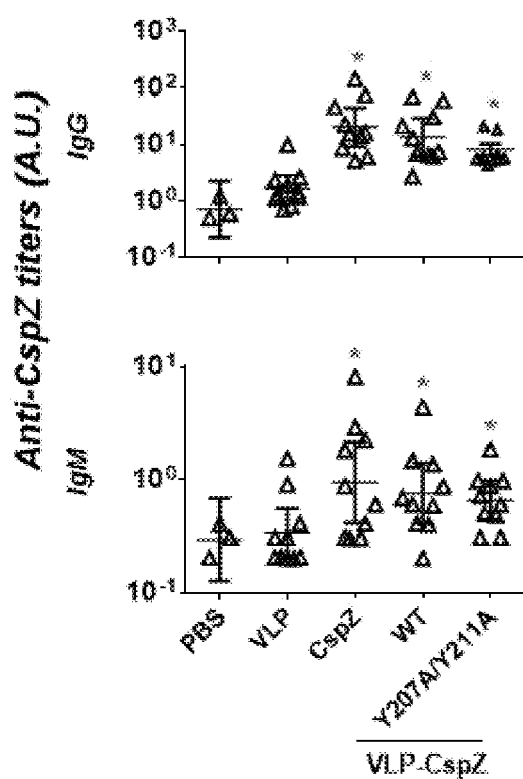
FIG. 4 shows that immunization of CspZ, VLP-CspZ, and VLP-CspZ-YA triggered undistinguishable antibody response against CspZ. C3H/HeN mice were inoculated i.p. with PBS, VLP, CspZ, VLP-CspZ, or VLP-CspZ-YA, and the serum was obtained at 42 days post inoculation. The levels of IgG (top panel) and IgM (bottom panel) against CspZ were determined using quantitative ELISA. Data shown are the mean±standard deviation of three (PBS) or ten (all others) mice per group. Statistical significance ($p<0.05$) of differences in antibody titers relative to PBS-inoculated mice was determined using a one-way ANOVA test and are indicated ("*").

Vaccinating mice with CspZ, VLP-CspZ, or VLP-CspZ-YA induced similar levels of anti-CspZ antibodies. To examine whether the conjugation of CspZ with VLP and/or the elimination the ability of CspZ to bind FH enhances its immunogenicity, mice were immunized with PBS, VLP, CspZ, VLP-CspZ, or VLP-CspZ-YA. FIG. 1. The levels of antibodies against CspZ in the sera from these mice were measured quantitatively using ELISA. As expected, the titers of anti-CspZ IgG and IgM in VLP-treated mice were not different from PBS-treated mice. FIG. 4. Vaccination with CspZ elicited antibody response against CspZ, which was five-(for IgM) to ten-fold (for IgG) higher than PBS- or VLP-inoculated mice. FIG. 4. VLP-CspZ and VLP-CspZ-YA vaccinations also induced anti-CspZ antibodies (five-(for IgM) to ten-fold (for IgG) greater than PBS- and VLP-treated mice; FIG. 4). However, the anti-CspZ antibody responses induced by CspZ, VLP-CspZ, and VLP-CspZ-YA vaccination were not different, suggesting that conjugating CspZ to VLP or eliminating FH-binding activity of this protein does not increase the total antibody response against CspZ.

Figures 5A, 5B:
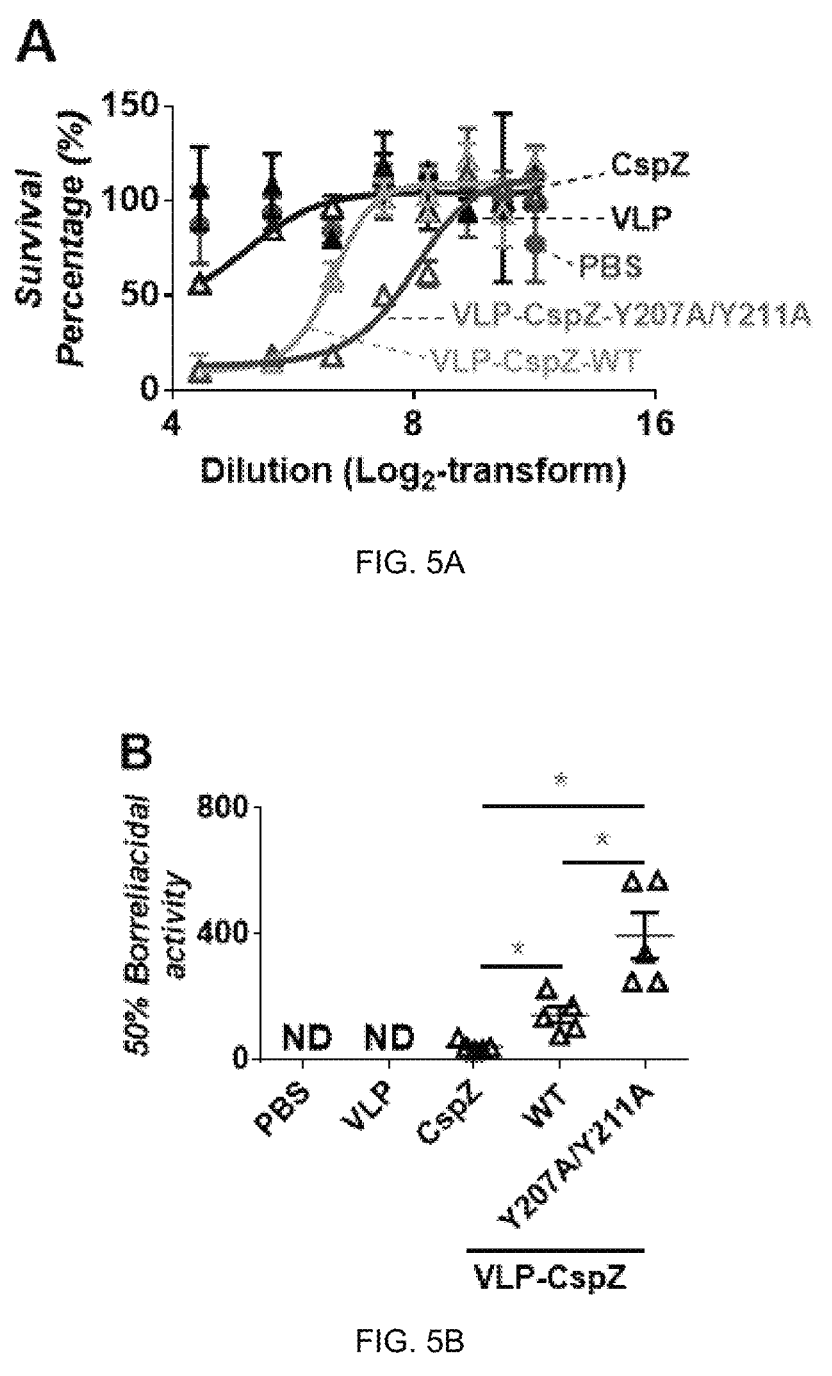

Sera from mice immunized with VLP-CspZ-YA eradicated spirochetes more effectively than that from CspZ- or VLP-CspZ-inoculated mice. Although antibody titers obtained with unmodified and modified CspZ were similar, the ability of these antibodies in killing spirochetes may be different. Thus whether eliminating FH binding or VLP conjugation to CspZ would elicit more robust borreliacidal antibody responses was examined. Stepwise dilutions of serum from PBS-, VLP-, CspZ-, VLP-CspZ-, or VLP-CspZ-YA-inoculated mice were mixed with guinea pig complement and B. burgdorferi, and the levels of spirochete survival were quantified after 24-hour incubation. The 50% borreliacidal activity (the dilution rate in which 50% of spirochetes are eliminated) was calculated to quantitatively compare the borreliacidal differences of these sera. Whereas the serum from the PBS- or VLP-inoculated mice was incapable of eradicating spirochetes, the serum from CspZ-, VLP-CspZ-, or VLP-CspZ-YA-immunized mice killed B. burgdorferi in a dose-dependent manner. FIG. 5A. The serum from CspZ-vaccinated mice killed 50% of spirochetes at an average dilution rate of 1:43, whereas diluting the serum from VLP-CspZ-immunized mice at an average of 1:143 eliminated 50% of B. burgdorferi (three-fold more effective than that from CspZ-vaccinated mice; FIG. 5A, Table 1).

TABLE 1

Quantitative determination of borreliacidal activity in the serum obtained from CspZ-, VLP- or PBS-inoculated mice.

| Vaccination | 50% borreliacidal titer |
|---|---|
| PBS[a] | NI[c] |
| VLP[b] | NI |
| CspZ[b] | 43.02 ± 16.23 |
| VLP-CspZ[b] | 143.24 ± 57.85 |
| VLP-CspZ-YA[b] | 395.81 ± 163.72 |

Data shown are mean ± standard error of the mean
[a]Three mice per group
[b]Five mice per group
[c]NI: No inhibition (no killing)

Interestingly, the serum from the VLP-CspZ-YA-immunized mice eradicated 50% of spirochetes at the average dilution rate of 1:395, which was nine- or three-fold more effective than that from the mice immunized with CspZ or VLP-CspZ, respectively. FIGS. 5A and 5B; Table 1. Thus, vaccination of VLP-CspZ-YA induced antibodies with the greatest borreliacidal activity.

Passive immunization of naïve mice with serum from VLP-CspZ-YA-vaccinated mice prevented Lyme disease. It was next determined if passively immunizing mice with serum containing anti-CspZ antibodies with greater borreliacidal activity provides more effective protection against Lyme infection. Naïve mice were passively-immunized with serum collected from VLP, CspZ, VLP-CspZ, or VLP-CspZ-YA actively-immunized mice or the pre-immune mouse serum, and then infected with B. burgdorferi. FIG. 1A. As expected, the pre-immune mouse serum did not protect mice against B. burgdorferi infection (0/6; Table 2).

TABLE 2

Protection against B. burgdorferi in mice passively immunized with serum raised from CspZ- or VLP-immunized mice.

| Immunogen | No. of tissue culture positive/total[a] | | | | | No. of mice protected/total[a,b] | p value[c] |
| | Inoc. site | Bladder | Heart | Joint | Ear | | |
|---|---|---|---|---|---|---|---|
| Preimmune serum | 6/6 | 6/6 | 6/6 | 6/6 | 6/6 | 0/6 | |
| VLP | 6/6 | 6/6 | 6/6 | 6/6 | 5/6 | 0/6 | 1.00 |
| CspZ | 6/6 | 5/6 | 6/6 | 4/6 | 4/6 | 0/6 | 1.00 |
| VLP-CspZ | 4/6 | 4/6 | 4/6 | 4/6 | 4/6 | 2/6 | 0.22 |
| VLP-CspZ-YA | 0/6 | 0/6 | 0/6 | 0/6 | 0/6 | 6/6 | 0.002 |

[a]Combined two trials.
[b] Mice were considered infected (not protected) when at least one culture was positive.
[c]One-tailed Fisher Exact Probability Test, Compared to the mice inoculated with pre-immune mouse serum.

The serum from VLP-immunized mice was unable to protect any passively-immunized mice from being infected by spirochetes (0/6; Table 2). Similarly, no protection was observed in any mice passively-immunized with serum from CspZ-vaccinated mice (0/6; Table 2). Passive immunization with serum from VLP-CspZ-vaccinated mice prevented Lyme infections in 33% of mice (2/6), but this protection efficiency is not statistically different from that in pre-immune serum inoculated mice (p=0.22; Table 2). Interestingly, passively immunizing with the serum obtained from VLP-CspZ-YA-vaccinated mice protected 100% of mice from Lyme infection (6/6; Table 2), and such efficiency is significantly greater than that in pre-immune mouse serum-inoculated mice (p=0.002; Table 2). These results suggest that the serum from the mice vaccinated with VLP-CspZ-YA completely protects naïve mice from Lyme infection via passive immunization.

Figure 6:
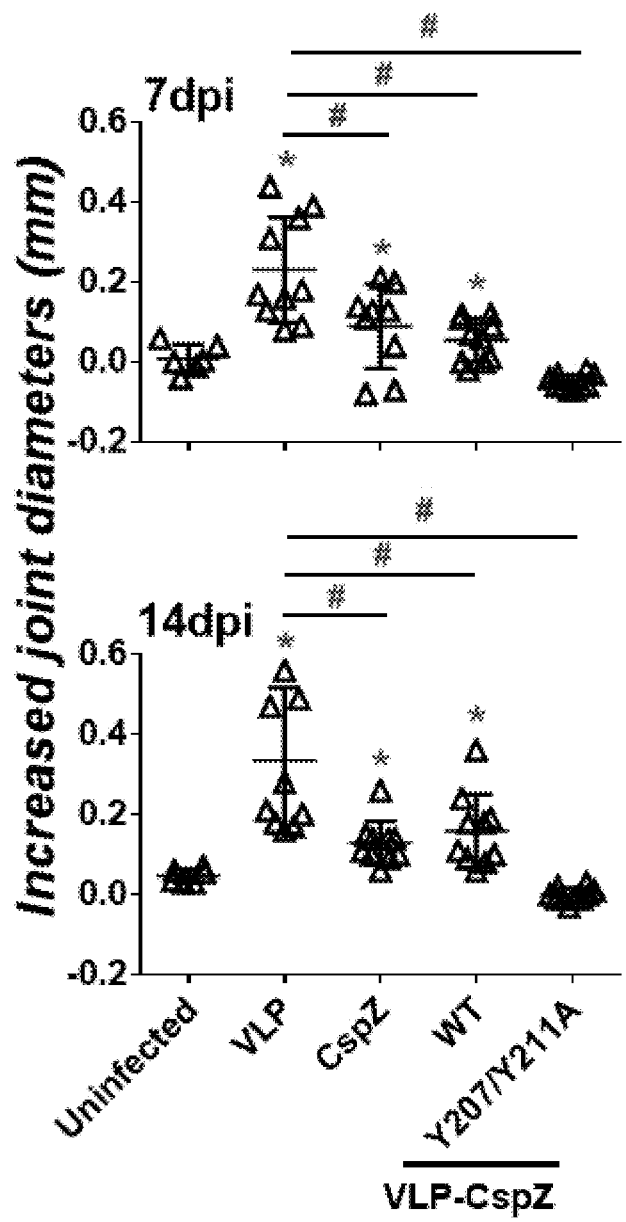
FIG. 6 demonstrates that immunizing mice with VLP-CspZ-YA prevented joint swelling compared to VLP or VLP-CspZ vaccination. C3H/HeN mice were vaccinated i.p. with VLP, CspZ, VLP-CspZ, or VLP-CspZ-YA prior to infection with $10^4$ *B. burgdorferi* strain B31-A3. The diameters of tibiotarsus joints were measured at (top panel) 7 and (bottom panel) 14 days' post-infection, and from uninfected mice of the same age. The increased joint diameters were derived from subtracting the group average tibiotarsus joint diameter prior to infection (0 days' post-infection). Data shown are the mean±standard deviation of six (uninfected) or ten (all others) mice per group. Statistical significance (p<0.05) of differences in tibiotarsus joint diameters of each group relative to uninfected mice were determined using a one-way ANOVA test and post-hoc analysis and are indicated ("*"). Significant differences (p<0.05) between infected groups are indicated ("#").

Immunization with VLP-CspZ-YA provided greater protection from Lyme-associated arthritis than vaccination with CspZ or VLP-CspZ. To test whether the CspZ antibodies with greater borreliacidal activity confer more efficient protection from Lyme arthritis via active immunization, mice actively immunized with VLP, CspZ, VLP-CspZ, or VLP-CspZ-YA were infected with B. burgdorferi. Joint diameters were measured at 7 and 14 days post infection (FIG. 1B), as Lyme-induced joint swelling is detectable as early as these time points. As expected, VLP-inoculated mice displayed joint swelling, with the levels most apparent at 7 and 14 days post infection (at least eight-fold greater joint diameters than uninfected mice; FIG. 6). CspZ and VLP-CspZ vaccinations reduced joint swelling at these time points (approximately two-fold less than the mice inoculated with VLP). However, the joint diameters were still significantly greater than that of uninfected mice (p<0.05), suggesting that CspZ or VLP-CspZ vaccination was incapable of completely alleviating the joint swelling caused by Lyme infection. FIG. 6. Interestingly, the joint diameters in the mice immunized with VLP-CspZ-YA were at least three-fold less than VLP-immunized mice at 7 and 14 days post infection, but were no different than uninfected mice. FIG. 6. These results show that VLP-CspZ-YA protects mice from Lyme-associated joint swelling.

Figure 7:
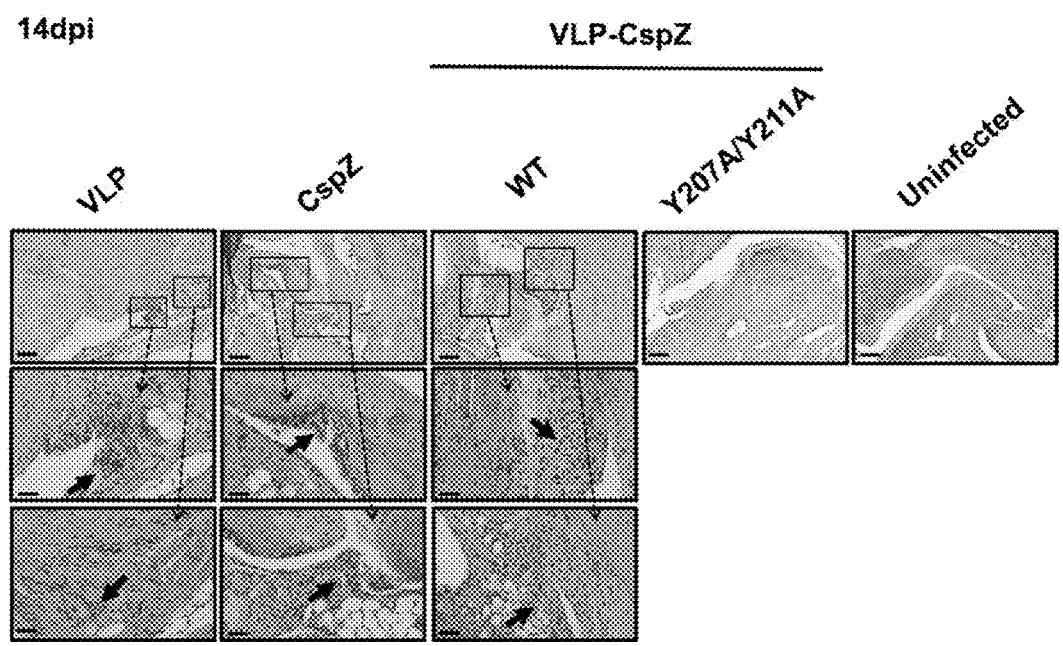
FIG. 7 demonstrates that VLP-CspZ-YA immunization prevents Lyme arthritis in *B. burgdorferi*-infected C3H/HeN mice at levels similar to uninfected mice. C3H/HeN mice were vaccinated i.p. with VLP, CspZ, VLP-CspZ, or VLP-CspZ-YA and subsequently infected with $10^4$ *B. burgdorferi* strain B31-A3. Tibiotarsus joints were collected 14 days post infection, and from uninfected mice of the same age. To assess inflammation, tissues were fixed and stained with hematoxylin and eosin. Top panels are lower-resolution images (joint, ×10 [bar, 160 µm]); bottom panels are higher-resolution images (joint, 2×20 [bar, 80 µm]) of selected areas (insets in top panels). Arrows indicate infiltration of immune cells.

Additionally, the severity of the arthritis in the mice vaccinated with VLP, CspZ, VLP-CspZ, or VLP-CspZ-YA at 14 days post infection was histologically examined. As expected, the VLP-inoculated mice developed significant arthritis with inflammation at the joint, in which inflammatory cells infiltrated around the synovium. FIG. 7. A similar arthritis phenotype was observed in CspZ- or VLP-CspZ-vaccinated mice. FIG. 7. However, VLP-CspZ-YA-vaccinated mice did not develop arthritis, with histopathology revealing inflammation similar to uninfected mice. FIG. 7. These results indicate that vaccination of VLP-CspZ-YA prevents mice from developing arthritis during Lyme infection.

Figure 8:
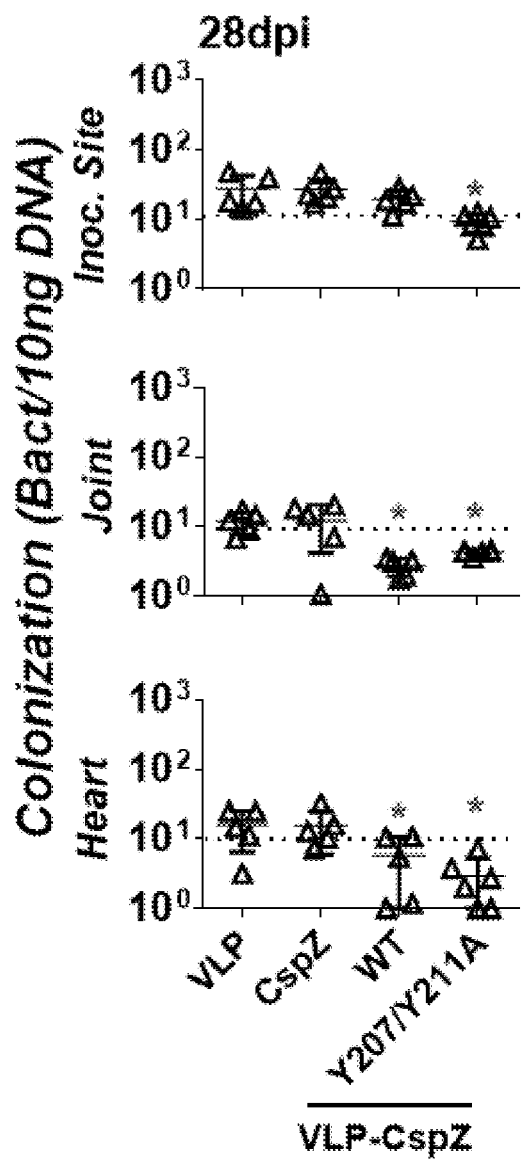
FIG. 8 demonstrates that vaccinating mice with VLP-CspZ-YA eliminated *B. burgdorferi* tissue colonization compared to VLP or VLP-CspZ immunization. C3H/HeN mice were immunized i.p. with VLP, CspZ, VLP-CspZ, or VLP-CspZ-YA and subsequently infected with $10^4$ *B. burgdorferi* strain B31-A3. Spirochete colonization at inoculation site of skin ("inoc. site", top panel), knee joint ("joint", middle panel), and heart ("heart", bottom panel) was quantitatively measured 28 days post infection. Colonization was derived by normalizing the number of spirochetes detected by qPCR to 10 ng total DNA. Data shown are the mean±standard deviation, of five (VLP, CspZ, VLP-CspZ) or six (VLP-CspZ-YA) mice. Statistical significance (p<0.05) of differences in bacterial burden relative to VLP-immunized mice was determined using a one-way ANOVA test and post-hoc analysis and are indicated ("*")

Immunization with VLP-CspZ-YA conferred greater protection against B. burgdorferi tissue colonization than CspZ or VLP-CspZ vaccination. To evaluate if vaccination with modified CspZ conjugated to VLP clears spirochete tissue colonization at later stages of infection, mice were immunized with VLP, CspZ, VLP-CspZ, or VLP-CspZ-YA, prior to infection with B. burgdorferi. Bacterial burdens were quantitatively assessed in tissues from these mice at 28 days post infection using qPCR. FIG. 1B. B. burgdorferi colonized the inoculation site of skin, joints, and heart of VLP-inoculated mice. FIG. 8. Spirochete burdens in these tissues from CspZ-immunized mice were no different than that from VLP-inoculated mice. FIG. 8. The bacterial burdens in VLP-CspZ-immunized mice were below the detection limit in the heart and joints (detection limit=10 bacteria copies per 10 ng DNA; Table 3) and 2.7 to 4.4-fold lower than VLP-immunized mice (p<0.05; FIG. 8).

TABLE 3

B. burgdorferi burden in tissues from CspZ-, VLP- or PBS-inoculated mice at 28 days post infection.

| | Colonization (Bacteria/10 ng DNA) | | |
|---|---|---|---|
| Immunogen | Inoculation Site | Joint | Heart |
| VLP[a] | 27.54 ± 15.27 | 12.01 ± 1.90 | 15.73 ± 4.15 |
| CspZ[a] | 26.92 ± 5.06 | 12.32 ± 3.63 | 15.62 ± 4.34 |
| VLP-CspZ[a] | 19.63 ± 2.93 | 2.72 ± 0.35* | 5.77 ± 2.13* |
| VLP-CspZ-YA[b] | 9.30 ± 1.12* | 4.29 ± 0.15* | 2.94 ± 0.95* |

Data shown are mean ± standard deviation of the number of B. burgdorferi present as determined from qPCR, based on the data in FIG 6.
[a]Five mice per group
[b]Six mice
*Bacterial burden are below the limit of detection (10 bacteria/10 ng DNA), and significantly lower (p < 0.05) than VLP-vaccinated mice as determined with one-way ANOVA test and post-hoc analysis.

However, there was no difference in the bacterial burden at the inoculation sites of VLP-CspZ and VLP-inoculated mice. FIG. 8. Vaccination of VLP-CspZ-YA resulted in undetectable bacterial burdens at the inoculation site, joints, and heart during Lyme infection that were 2.8 to 5.4-fold lower than CspZ- and VLP-inoculated mice (p<0.05; FIG. 8), indicating VLP-CspZ-YA protects mice from being colonized by B. burgdorferi.

B. burgdorferi CspZ was chosen as a potential vaccine candidate because of its antigenicity and its ability to facilitate evasion of complement system. While vaccination with CspZ elicits a robust antibody response, it does not protect mice from Lyme infection, possibly due to insufficient functional antibodies (i.e., bactericidal). The efficacy of CspZ as a vaccine against Lyme disease was thus re-evaluated by conjugating CspZ to VLP to generate VLP-CspZ, and combined this approach with eliminating the FH-binding activity of CspZ to generate VLP-CspZ-YA (Siegel et al., 2008). Without being limited to or by any possible theory or hypothesis as to mechanism of action, conjugating antigens to the highly repetitive structures of VLPs may alter the topology of these antigens and may eventually allow B cells to more efficiently recognize the epitopes and develop greater levels of antibodies with enhanced bactericidal activity (Hinton et al., 2008; Rynda-Apple et al., 2014). As disclosed herein, though neither VLP-CspZ nor VLP-CspZ-YA triggered greater titers of anti-CspZ antibodies compared to mice immunized with CspZ, immunizing mice with either of these VLP-CspZ proteins induced antibodies with robust levels of bacterial killing activity.

Discloses herein is complete in vivo protection against Lyme disease from passive immunization with VLP-CspZ-YA, but not CspZ or VLP-CspZ. During active immunization, whereas no significant difference in joint swelling is observed between unvaccinated- and CspZ-vaccinated mice after infection of B. burgdorferi, results disclosed herein showed that CspZ vaccination provided minor protection from joint swelling compared to VLP-vaccinated mice. Vaccination with CspZ or VLP-CspZ did not prevent arthritis, which implies that the bactericidal ability of the antibodies induced by either of these proteins were insufficient in alleviating Lyme associated arthritis, whereas vaccination of VLP-CspZ-YA prevented both joint swelling and arthritis.

Active immunization of unmodified CspZ was incapable of preventing *B. burgdorferi* colonization at both proximal (inoculation site) and distal mouse tissues (heart and joints). Inoculating mice with either VLP-CspZ or VLP-CspZ-YA cleared *B. burgdorferi* colonization at distal tissues. However, VLP-CspZ-YA vaccination cleared colonization at the inoculation site while VLP-CspZ immunization did not. This is the first demonstration of the ability of CspZ with eliminated FH-binding to prevent infection in vivo.

In other examples disclosed below, an immunogenic composition including a modified CspZ peptide sequence as disclosed herein protects against *B. burgdorferi* infection without requiring administration to a subject in the presence of VLP. However, VLP conjugation may enhance the efficacy of a modified CspZ based immunogenic composition as disclosed herein to prevent *B. burgdorferi* colonization or disease manifestations.

Figure 10:
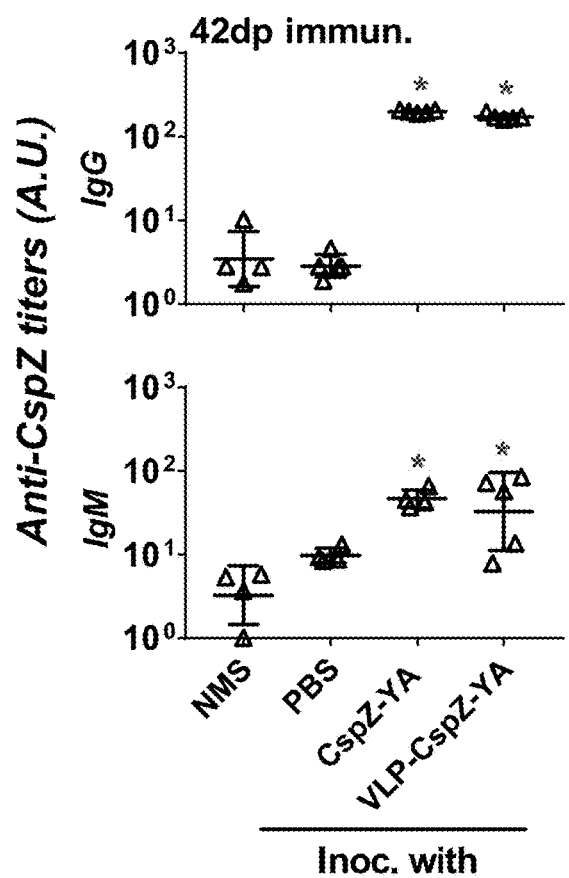
FIG. 10 is a graph demonstrating that immunization of CspZ-YA, VLP-CspZ-YA triggered undistinguishable levels of antibody against CspZ. Five C3H/HeN mice were inoculated i.d. with PBS, CspZ-YA, or VLP-CspZ-YA, and the serum was obtained at 42 days post inoculation. The serum collected from four unvaccinated C3H/HeN mice was included as negative control ("NMS", normal mouse serum). The levels of IgG (top panel) and IgM (bottom panel) against CspZ were determined using quantitative ELISA as described in Materials and Methods. Data shown are the geometric mean±geometric standard deviation of four (NMS) or five (all others) mice per group. Statistical significances (p<0.05) of differences in antibody titers relative to negative control group of mice were determined using a one-way ANOVA test and are indicated ("*").

Vaccination of CspZ-YA or VLP-CspZ-YA triggered similar levels of antibodies. Vaccination of VLP-CspZ-YA triggers robust levels of antibody immune response. Essentiality of VLP in enhancing this antigen to produce antibodies was further evaluated. The mice were thus inoculated with PBS buffer (negative control), CspZ-YA, or VLP-CspZ-YA (FIG. 9). These mice were inoculated intradermally. After two boosters followed by initial immunization of these antigens, the anti-CspZ IgG and IgM antibody titers in these mice's sera were determined. As expected, close to undetectable levels of IgG or IgM antibodies were found in serum from PBS-inoculated mice, no different from normal mouse serum (FIG. 10). The serum from the mice vaccinated with either CspZ-YA or VLP-CspZ-YA contained approximately 8- and 100-fold greater levels of IgG and IgM, respectively, compared to negative control mouse serum (FIG. 10). However, The IgG or IgM titers in the serum from CspZ-YA- or VLP-CspZ-YA-immunized mice were undistinguishable, indicating VLP conjugation is not essential to enhance the antigenicity of CspZ-YA.

Figures 11A, 11B:
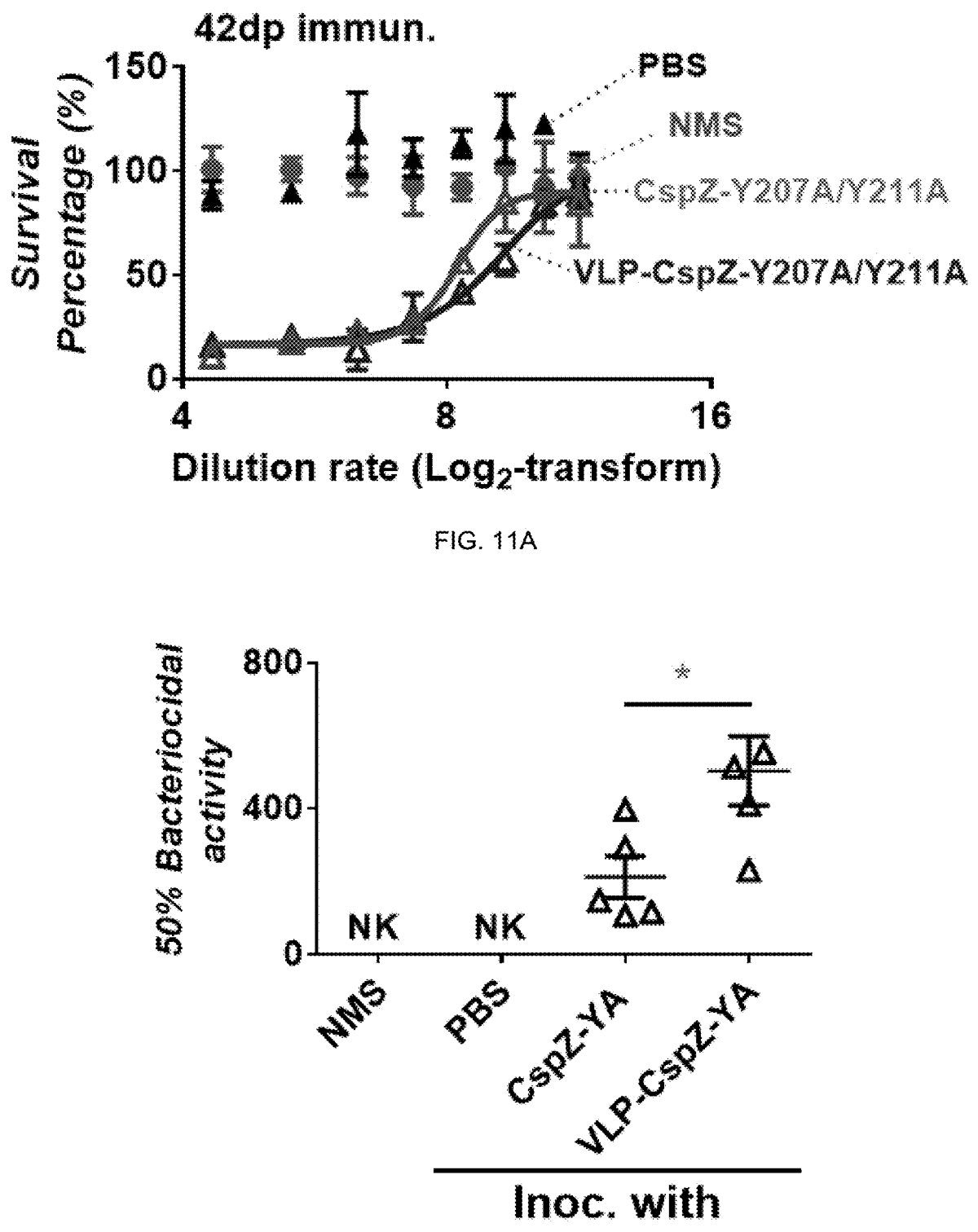

Sera from mice immunized with VLP-CspZ-YA eradicated *B. burgdorferi* more efficiently than that from CspZ-YA-vaccinated mice. Whether conjugation of VLP to CspZ-YA allows this protein to trigger the antibody with greater levels of bactericidal ability compared to unconjugated CspZ-YA was determined. The serum from PBS-, CspZ-YA, or VLP-CspZ-YA-inoculated mice was serially diluted and mixed with guinea pig complement and *B. burgdorferi*. Viability of the spirochetes after 24-hour incubation to obtain the 50% borreliacidal activity (the dilution rate in which 50% of spirochetes are eliminated) was measured. Serum from PBS-inoculated mice, similar to normal mouse serum, is unable to eliminate spirochetes (FIGS. 11A and 11B). The serum from CspZ-YA-immunized mice killed 50% of spirochetes at an average dilution rate of 1:212 (FIGS. 11A and 11B and Table 4).

TABLE 4

Quantitative determination of borreliacidal activity in the serum obtained from CspZ-, VLP- or PBS-inoculated mice.

| Vaccination | 50% borreliacidal titer |
| --- | --- |
| NMS[a] | NK[c] |
| PBS[b] | NK |
| VLP-CspZ-YA[b] | 504.22 ± 94.93 |
| CspZ-YA[b] | 212.74 ± 57.11 |

Data shown are mean ± standard error of the mean
[a]Normal mouse serum, three mice per group
[b]Five mice per group
[c]NK: No killing The serum from VLP-CspZ-YA-vaccinated mice eradicated 50% of *B. burgdorferi* at an average dilution rate of 1:504, 2.3-fold greater than the serum from CspZ-YA-immunized mice (FIGS. 11A and 11B and Table 4). These results suggest that the anti-CspZ antibody triggered by VLP-CspZ-YA vaccination may display greater borreliacidal activity than that induced by CspZ-YA immunization.

Vaccination of CspZ-YA or VLP-CspZ-YA prevents mice from Lyme disease associated arthritis. The ability of CspZ-YA and VLP-CspZ-YA as vaccines to prevent arthritis caused by *B. burgdorferi* infection through tick feeding was investigated. The mice were inoculated with each of these proteins or PBS (negative control) followed by being challenged via the feeding of nymphal ticks carrying *B. burgdorferi* (FIG. 9). The mice inoculated with PBS and then fed by uninfected nymphs were included as negative control (uninfected mice). At 14- and 21-days post tick feeding, PBS-inoculated and *B. burgdorferi*-infected mice developed apparent joint swelling, approximately 1.6 to 2-fold greater than uninfected mice (FIG. 4). However, the joint size of either CspZ-YA- or VLP-CspZ-YA-immunized mice was no different from that in uninfected mice at these time points (FIG. 4). These results suggest that vaccination of each of these proteins prevents the joint swelling caused by *B. burgdorferi* infection via tick feeding.

Figure 12:
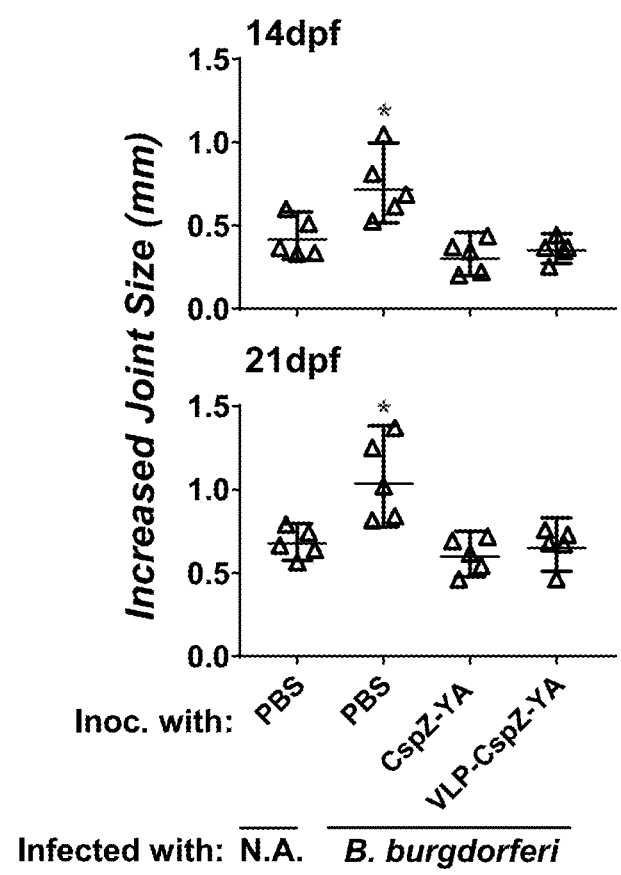
FIG. 12 is a graph showing that the levels of joint size in CspZ-YA- or VLP-CspZ-YA-immunized and *B. burgdorferi*-infected mice were no different from that in uninfected mice. Five C3H/HeN mice were inoculated i.d. with PBS, CspZ-YA, or VLP-CspZ-YA prior to be challenged with *B. burgdorferi* strain B31-A3 via nymph feeding. The diameters of tibiotarsus joints were measured at (top panel) 14 and (bottom panel) 21 days post-infection, and from the PBS-inoculated five mice fed by uninfected nymphs ("PBS", uninfected mice). The increased joint diameters were derived from subtracting the group average tibiotarsus joint diameter prior to infection (0 days' post-feeding). Data shown are the mean±standard deviation of five mice per group. Statistical significance (p<0.05) of differences in tibiotarsus joint diameters of each group relative to uninfected mice were determined using a one-way ANOVA test and post-hoc analysis and are indicated ("*"). Significant differences (p<0.05) between infected groups are indicated ("#").
Figure 13A:
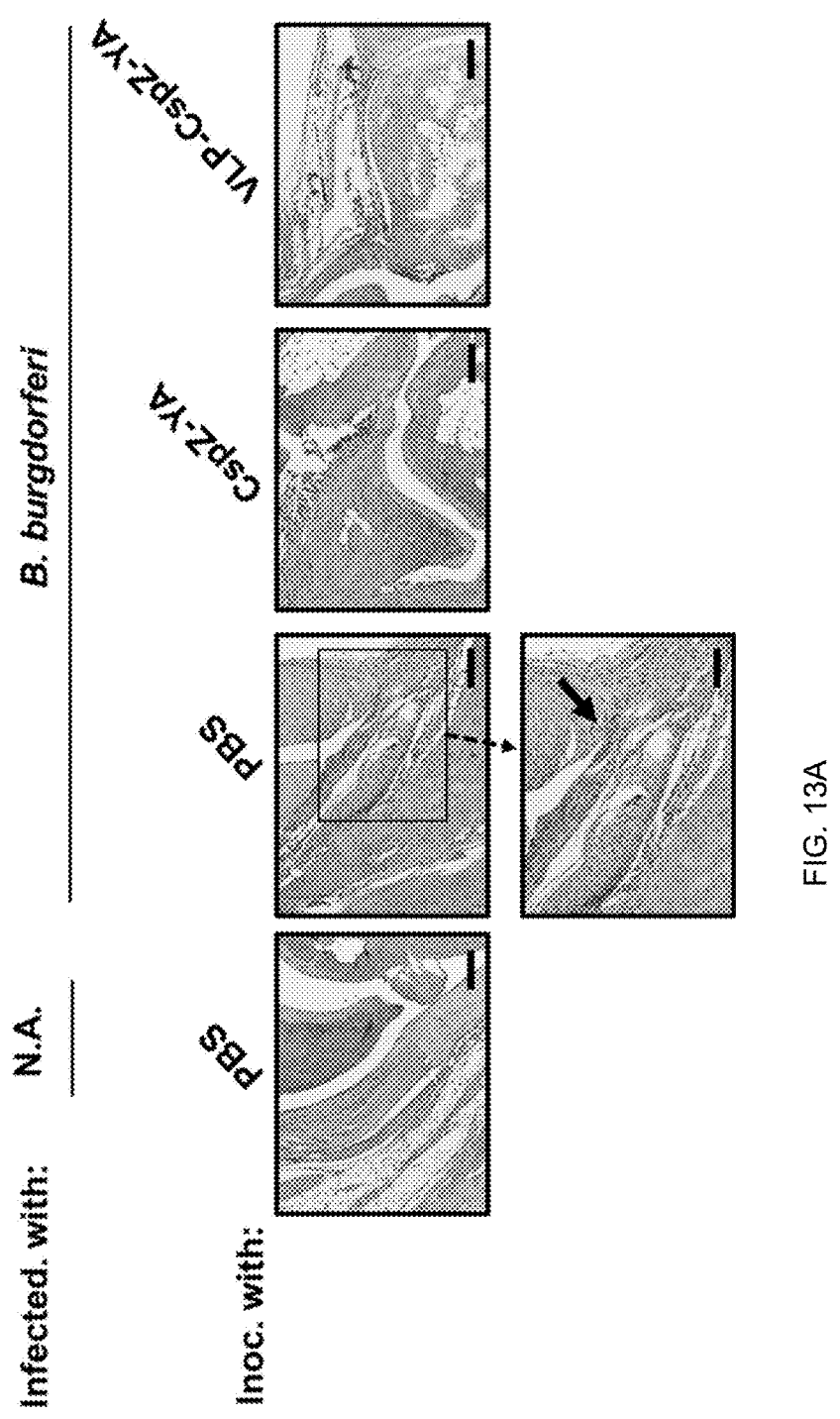
Figure 13B:
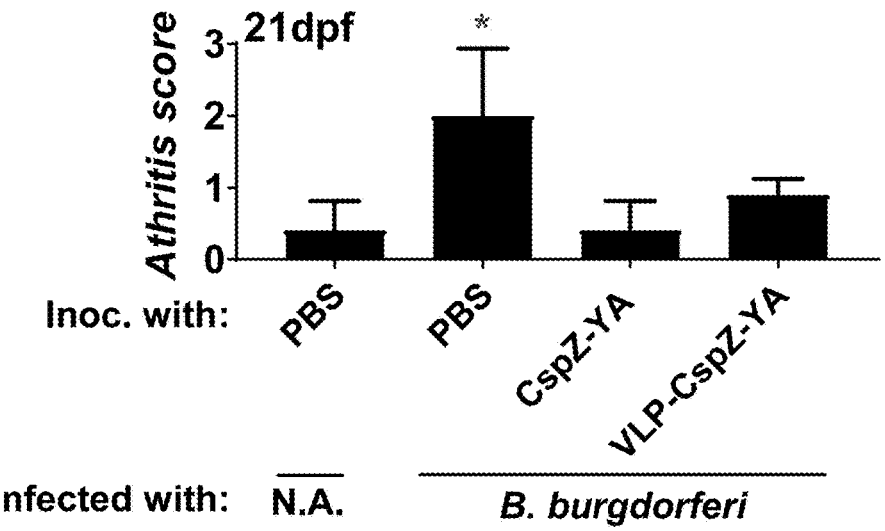

Levels of arthritis in the mice inoculated with CspZ-YA, VLP-CspZ-YA, or PBS at 21 days post tick feeding were histologically evaluated (FIG. 12). Inflammation at joints of PBS-inoculated and *B. burgdorferi*-infected mice were observed, in which inflammatory cells such as neutrophils infiltrated around the synovium (FIG. 13A). The arthritis score of these mice (2±0.93) was significantly greater than that of uninfected mice (0.4±0.41, p<0.05) (FIG. 13B). However, the CspZ-YA or VLP-CspZ-YA-vaccinated mice did not develop arthritis (FIG. 13A), with arthritis scores no different from that in uninfected mice (FIG. 5B). These results clearly indicate the ability of CspZ-YA and VLP-CspZ-YA as vaccines to prevent Lyme disease associated arthritis during the tick-borne *B. burgdorferi* infection.

Figure 14:
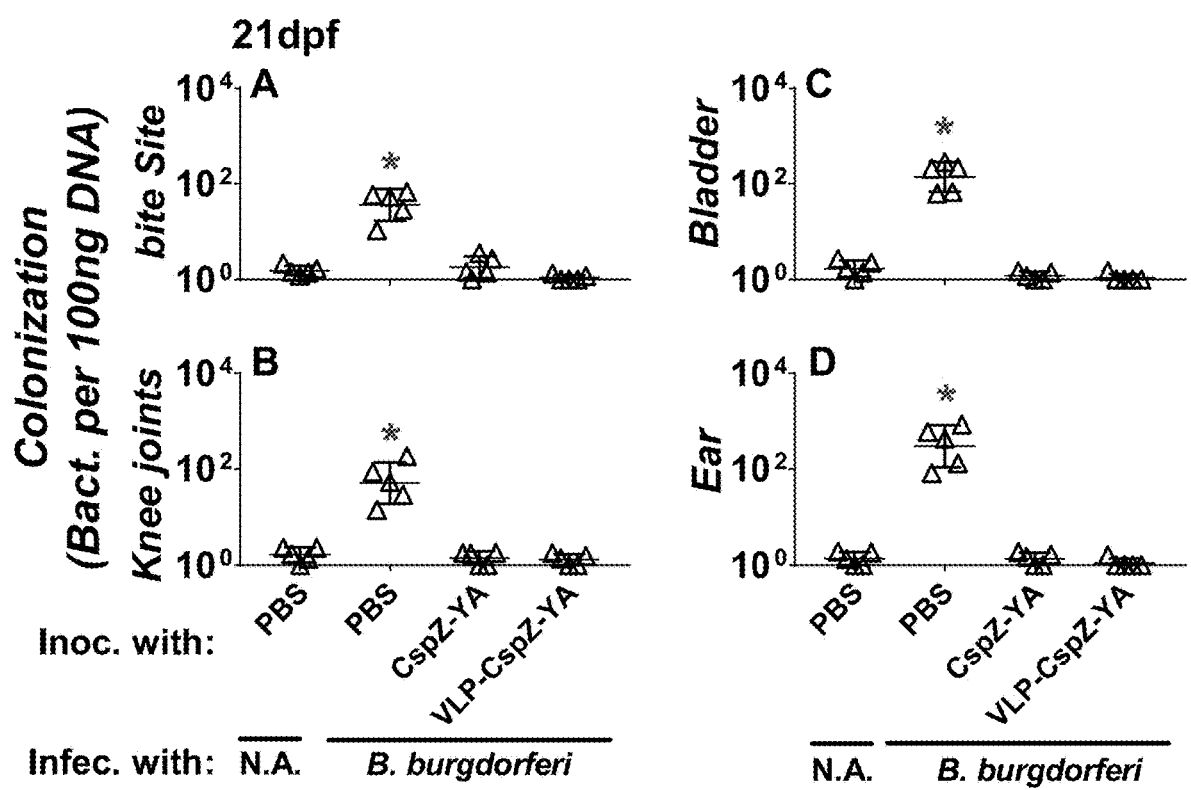
FIG. 14 is a graph demonstrating that vaccinating mice with CspZ-YA or VLP-CspZ-YA eliminated *B. burgdorferi* tissue colonization compared to uninfected mice. Five C3H/HeN mice were inoculated i.d. with PBS, CspZ-YA, or VLP-CspZ-YA and subsequently fed by nymphs carrying *B. burgdorferi* strain B31-A3. Five mice inoculated with PBS and fed by uninfected nymphs were also included as negative control (uninfected mice). Spirochete colonization at (A) tick biting sites of skin ("bite site"), (B) knee joints, (C) bladder, and (D) heart was quantitatively measured 21 days post tick feeding. Colonization was derived by normalizing the number of spirochetes detected by qPCR to 100 ng total DNA. Data shown are the geometric mean±geometric standard deviation, of five mice. Statistical significance (p<0.05) of differences in bacterial burden relative to uninfected mice was determined using a one-way ANOVA test and post-hoc analysis and are indicated ("*").

Immunization of CspZ-YA or VLP-CspZ-YA prevents mice from *B. burgdorferi* colonization during Lyme disease infection. The ability of CspZ-YA or VLP-CspZ-YA as vaccines to block spirochete colonization during Lyme disease infection was evaluated. Mice were inoculated with PBS, CspZ-YA, or VLP-CspZ-YA and then challenged mice with *B. burgdorferi*-infected nymphs. The mice administrated with PBS and fed by uninfected nymphs were included as control (uninfected mice). The bacterial burdens in different mouse tissues were collected at 21 days post tick feeding to determine the levels of spirochete colonization at these tissues. As expected, the bacterial burdens in the biting site of ticks, knee joints, bladder, and heart of uninfected mice were below detection limit (2 spirochetes per 100 ng DNA FIG. 14). *B. burgdorferi* was observed in these tissues (36 to 295 spirochetes per 100 ng DNA, FIG. 14), 24 to 226-fold greater than that obtained from uninfected mice (FIG. 14). However, spirochetes were undetectable in any of above-mentioned tissues from CspZ-YA- or VLP-CspZ-YA-vaccinated mice (FIG. 14). These results indicate that inoculation of these antigens allows mice to be immune to *B. burgdorferi* colonization via tick feeding.

Although several embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as recited in the claims that follow.

What is claimed is:

1. An immunogenic composition, comprising
a peptide, wherein consecutive amino acids of the peptide comprise consecutive amino acids of SEQ ID NO:1 and the consecutive amino acids of SEQ ID NO:1 are selected from the group consisting of amino acids 186-193 of SEQ ID NO:1, 187-194 of SEQ ID NO:1, 188-195 of SEQ ID NO:1, 189-196 of SEQ ID NO:1, and any combination of two or more of the foregoing, wherein one or both of amino acids 189 and 193 of SEQ ID NO:1 comprises alanine or is independently substituted with any other amino acid except tyrosine, and
one or more adjuvant, wherein at least one of the one or more adjuvant is selected from an aluminum salt, AS04, AS03, monophosphoryl lipid A, poly(I:C), a CpG DNA adjuvant, MF59, an emulsion adjuvant comprising squalene and water, a combination adjuvant comprising block copolymer CRL-8300, squalene, a sorbitan monooleateor, N-[1-(2,3-Dioleoyloxy)propyl]-N,N,N-trimethylammonium salt (DOTAP), 3 β-[N—(N′,N′-dimethylaminoethane)-carbamoyl] cholesterol (DC-chol liposome), and a virosomal adjuvant.

2. The immunogenic composition of claim 1, wherein the consecutive amino acids of SEQ ID NO:1 are selected from the group consisting of amino acids 1-193 of SEQ ID NO:1, 1-194 of SEQ ID NO:1, 1-195 of SEQ ID NO:1, 1-196 of SEQ ID NO:1, and any combination of two or more of the foregoing, wherein one or both of amino acids 189 and 193 of SEQ ID NO:1 comprises alanine or is independently substituted with any other amino acid except tyrosine, and from 0 to 9 amino acids 1-185 of SEQ ID NO:1 is independently substituted with any other amino acid.

3. The immunogenic composition of claim 1, wherein the consecutive amino acids of SEQ ID NO:1 are selected from the group consisting of amino acids 186-218 of SEQ ID NO:1, 187-218 of SEQ ID NO:1, 188-218 of SEQ ID NO:1, 189-218 of SEQ ID NO:1, and any combination of two or more of the foregoing, wherein one or both of amino acids 189 and 193 of SEQ ID NO:1 comprises alanine or is independently substituted with any other amino acid except tyrosine, and 0 or 1 of amino acids 197-218 of SEQ ID NO:1 is substituted with any other amino acid.

4. The immunogenic composition of claim 1, wherein the consecutive amino acids of SEQ ID NO:1 are selected from the group consisting of amino acids 186-222 of SEQ ID NO:1, 187-222 of SEQ ID NO:1, 188-222 of SEQ ID NO:1, 189-222 of SEQ ID NO:1, and any combination of two or more of the foregoing, wherein one or both of amino acids 189 and 193 of SEQ ID NO:1 comprises alanine or is independently substituted with any other amino acid except tyrosine, and 0 or 1 of amino acids 197-222 of SEQ ID NO:1 is substituted with any other amino acid.

5. The immunogenic composition of claim 1, wherein the peptide comprises amino acids 1-218 of SEQ ID NO:1, wherein one or both of amino acids 189 and 193 of SEQ ID NO:1 comprises alanine or is independently substituted with any other amino acid except tyrosine, from 0 to 9 amino acids 1-185 of SEQ ID NO:1 is independently substituted with any other amino acid, and 0 or 1 of amino acids 197-218 of SEQ ID NO:1 is substituted with any other amino acid.

6. The immunogenic composition of claim 1, wherein the peptide comprises SEQ ID NO:1, wherein one or both of amino acids 189 and 193 of SEQ ID NO:1 comprises alanine or is independently substituted with any other amino acid except tyrosine, from 0 to 9 amino acids 1-185 of SEQ ID NO:1 is independently substituted with any other amino acid, and 0 or 1 of amino acids 197-222 of SEQ ID NO:1 is substituted with any other amino acid.

7. The immunogenic composition of claim 1, wherein the peptide comprises SEQ ID NO:1, wherein amino acids 189 and 193 of SEQ ID NO:1 comprise alanine.

8. The immunogenic composition of claim 1, wherein at least one of the one or more adjuvant is an aluminum salt.

9. The immunogenic composition of claim 1, wherein at least one of the one or more adjuvant is a CpG DNA adjuvant.

10. The immunogenic composition of claim 1, wherein at least one of the one or more adjuvant is a virosomal adjuvant.

11. A method of vaccinating a mammalian subject against *Borrelia burgdorferi*, comprising
administering to the subject the immunogenic composition of claim 1.

12. The method of claim 11, wherein the immunogenic composition comprises the immunogenic composition of claim 2.

13. The method of claim 11, wherein the immunogenic composition comprises the immunogenic composition of claim 3.

14. The method of claim 11, wherein the immunogenic composition comprises the immunogenic composition of claim 4.

15. The method of claim 11, wherein the immunogenic composition comprises the immunogenic composition of claim 5.

16. The method of claim 11, wherein the immunogenic composition comprises the immunogenic composition of claim 6.

17. The method of claim 11, wherein at least one of the one or more adjuvant is an aluminum salt.

18. The method of claim 11, wherein at least one of the one or more adjuvant is a CpG DNA adjuvant.

19. The method of claim 11, wherein at least one of the one or more adjuvant is a virosomal adjuvant.

20. The method of claim 11, wherein the subject is selected from a human, a cervid, and a rodent.

21. The method of claim 11, wherein the subject is a mouse.

22. The method of claim 11, wherein administering comprises administering orally.

23. An immunogenic composition, comprising
a peptide, wherein consecutive amino acids of the peptide comprise consecutive amino acids of SEQ ID NO:1 and the consecutive amino acids of SEQ ID NO:1 are selected from the group consisting of amino acids 186-193 of SEQ ID NO:1, 187-194 of SEQ ID NO:1, 188-195 of SEQ ID NO:1, 189-196 of SEQ ID NO:1, and any combination of two or more of the foregoing, wherein one or both of amino acids 189 and 193 of SEQ ID NO:1 comprises alanine or is independently substituted with any other amino acid except tyrosine, and
one or more adjuvant, wherein at least one of the one or more adjuvant comprises a peptide having the amino acid sequence of SEQ ID NO: 2.

* * * * *

SEQUENCE LISTING

<160> NUMBER OF SEQ ID NOS: 5

<210> SEQ ID NO 1
<211> LENGTH: 222
<212> TYPE: PRT
<213> ORGANISM: Artificial Sequence
<220> FEATURE:
<223> OTHER INFORMATION: Synthetic sequence

<400> SEQUENCE: 1

Ser Asp Val Ser Arg Leu Asn Gln Arg Asn Ile Asn Glu Leu Lys Ile
1               5                   10                  15

Phe Val Glu Lys Ala Lys Tyr Tyr Ser Ile Lys Leu Asp Ala Ile Tyr
            20                  25                  30

Asn Glu Cys Thr Gly Ala Tyr Asn Asp Ile Met Thr Tyr Ser Glu Gly
        35                  40                  45

Thr Phe Ser Asp Gln Ser Lys Val Asn Gln Ala Ile Ser Ile Phe Lys
    50                  55                  60

Lys Asp Asn Lys Ile Val Asn Lys Phe Lys Glu Leu Glu Lys Ile Ile
65                  70                  75                  80

Glu Glu Tyr Lys Pro Met Phe Leu Ser Lys Leu Ile Asp Asp Phe Ala
                85                  90                  95

Ile Glu Leu Asp Gln Ala Val Asp Asn Asp Val Ser Asn Ala Arg His
            100                 105                 110

Val Ala Asp Ser Tyr Lys Lys Leu Arg Lys Ser Val Val Leu Ala Tyr
        115                 120                 125

Ile Glu Ser Phe Asp Val Ile Ser Ser Lys Phe Val Asp Ser Lys Phe
    130                 135                 140

Val Glu Ala Ser Lys Lys Phe Val Asn Lys Ala Lys Glu Phe Val Glu
145                 150                 155                 160

Glu Asn Asp Leu Ile Ala Leu Glu Cys Ile Val Lys Thr Ile Gly Asp
                165                 170                 175

Met Val Asn Asp Arg Glu Ile Asn Ser Arg Ser Arg Ala Asn Asn Phe
            180                 185                 190

Ala Lys Lys Glu Ala Asp Phe Leu Gly Ala Ala Val Glu Leu Glu Gly
        195                 200                 205

Ala Tyr Lys Ala Ile Lys Gln Thr Leu Leu Gly Ser Gly Cys
    210                 215                 220

<210> SEQ ID NO 2
<211> LENGTH: 133
<212> TYPE: PRT
<213> ORGANISM: Escherichia phage Qbeta

<400> SEQUENCE: 2

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

```
Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 3
<211> LENGTH: 14
<212> TYPE: PRT
<213> ORGANISM: Artificial Sequence
<220> FEATURE:
<223> OTHER INFORMATION: Laboratory synthesized sequence

<400> SEQUENCE: 3

Met His His His His His His Glu Asn Leu Tyr Phe Gln Ser
1               5                   10

<210> SEQ ID NO 4
<211> LENGTH: 30
<212> TYPE: DNA
<213> ORGANISM: Borrelia burgdorferi

<400> SEQUENCE: 4
gtggatctat tgtattagat gaggctctcg                                  30

<210> SEQ ID NO 5
<211> LENGTH: 30
<212> TYPE: DNA
<213> ORGANISM: Borrelia burgdorferi

<400> SEQUENCE: 5
gccaaagttc tgcaacatta acacctaaag                                  30
```